(12) United States Patent
Yamamoto

(10) Patent No.: US 10,231,709 B2
(45) Date of Patent: **\*Mar. 19, 2019**

(54) ULTRASOUND DIAGNOSTIC APPARATUS, SIGNAL PROCESSING METHOD FOR ULTRASOUND DIAGNOSTIC APPARATUS, AND RECORDING MEDIUM

(71) Applicant: FUJIFILM Corporation, Tokyo (JP)

(72) Inventor: Hiroaki Yamamoto, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 765 days.

This patent is subject to a terminal disclaimer.

(21) Appl. No.: 14/859,874

(22) Filed: Sep. 21, 2015

(65) Prior Publication Data

US 2016/0007971 A1 Jan. 14, 2016

Related U.S. Application Data

(63) Continuation of application No. PCT/JP2014/052444, filed on Feb. 3, 2014.

(30) Foreign Application Priority Data

Mar. 22, 2013 (JP) ................................ 2013-060527

(51) Int. Cl.
 *A61B 8/08* (2006.01)
 *A61B 8/00* (2006.01)
 (Continued)

(52) U.S. Cl.
 CPC .......... *A61B 8/5207* (2013.01); *A61B 8/5269* (2013.01); *G01S 7/52077* (2013.01);
 (Continued)

(58) Field of Classification Search
 CPC ..... A61B 8/145; A61B 8/4444; A61B 8/4494; A61B 8/5207; A61B 8/5269;
 (Continued)

(56) References Cited

U.S. PATENT DOCUMENTS

| 8,485,977 | B2 | 7/2013 | Hirama | |
| 2009/0326377 | A1* | 12/2009 | Hirama | ............... G01S 7/52046 600/447 |
| 2015/0374339 | A1* | 12/2015 | Yamamoto | .......... G01S 7/52046 600/447 |

FOREIGN PATENT DOCUMENTS

| JP | 3-155840 A | 7/1991 |
| JP | 2004-195091 A | 7/2004 |

(Continued)

OTHER PUBLICATIONS

International Preliminary Report on Patentability and English translation of the Written Opinion of the International Searching Authority, dated Oct. 1, 2015, for International Application No. PCT/JP2014/052444.

(Continued)

*Primary Examiner* — Michael T Rozanski
(74) *Attorney, Agent, or Firm* — Birch, Stewart, Kolasch & Birch, LLP

(57) ABSTRACT

An object of the present invention is to provide an ultrasound diagnostic apparatus, a signal processing method, and a recording medium capable of appropriately superimposing data and obtaining high quality images when correcting data by superimposing a plurality of data. A transmission frequency of an ultrasonic beam is set according to a processing condition in a data processor, and second element data is generated using a plurality of first element data obtained by transmitting the ultrasonic beam at the transmission frequency.

10 Claims, 14 Drawing Sheets

(51) Int. Cl.
  *A61B 8/14*     (2006.01)
  *G01S 7/52*     (2006.01)
  *G01S 15/89*    (2006.01)

(52) U.S. Cl.
  CPC ........ *G01S 7/52095* (2013.01); *G01S 15/895* (2013.01); *G01S 15/8977* (2013.01); *A61B 8/145* (2013.01); *A61B 8/4444* (2013.01); *A61B 8/4494* (2013.01); *G01S 15/8997* (2013.01)

(58) Field of Classification Search
  CPC ............... G01S 15/895; G01S 15/8977; G01S 15/8997; G01S 7/52077; G01S 7/52095
  See application file for complete search history.

(56) References Cited

FOREIGN PATENT DOCUMENTS

JP    2009-240700 A    10/2009
JP    2012-157387 A     8/2012

OTHER PUBLICATIONS

Japanese Office Action for Japanese Application No. 2013-060527, dated May 31, 2016, with an English translation.
International Search Report, issued in PCT/JP2014/052444, dated Apr. 15, 2014.

\* cited by examiner

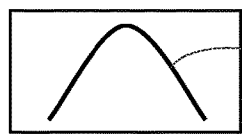
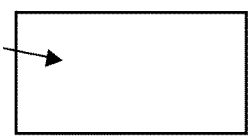
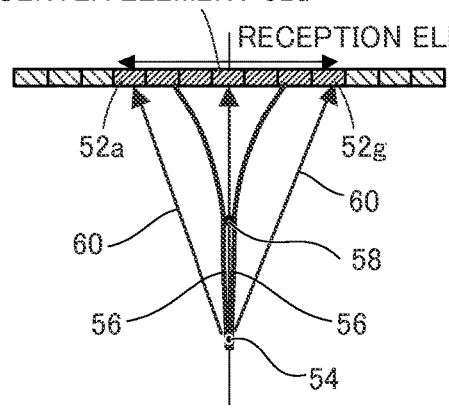
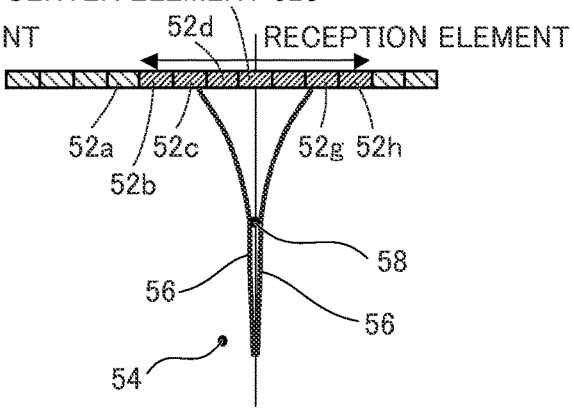
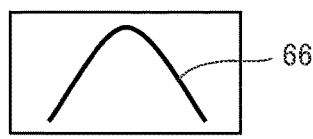
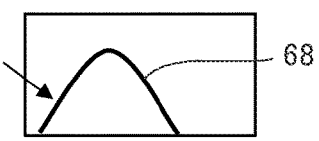
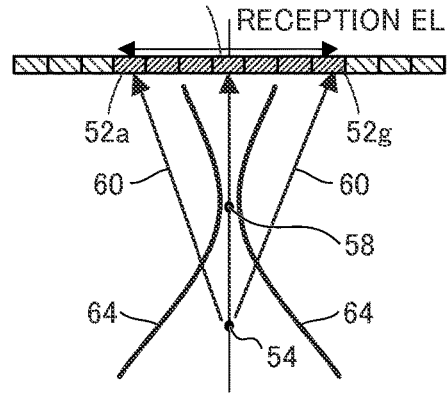
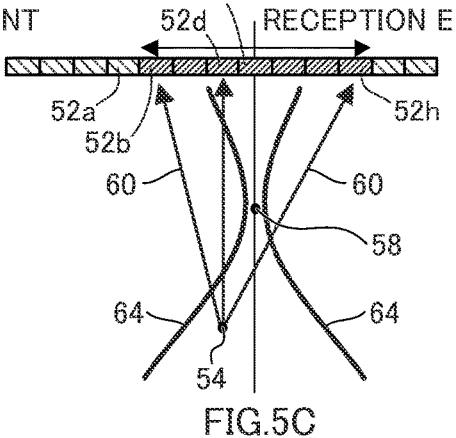

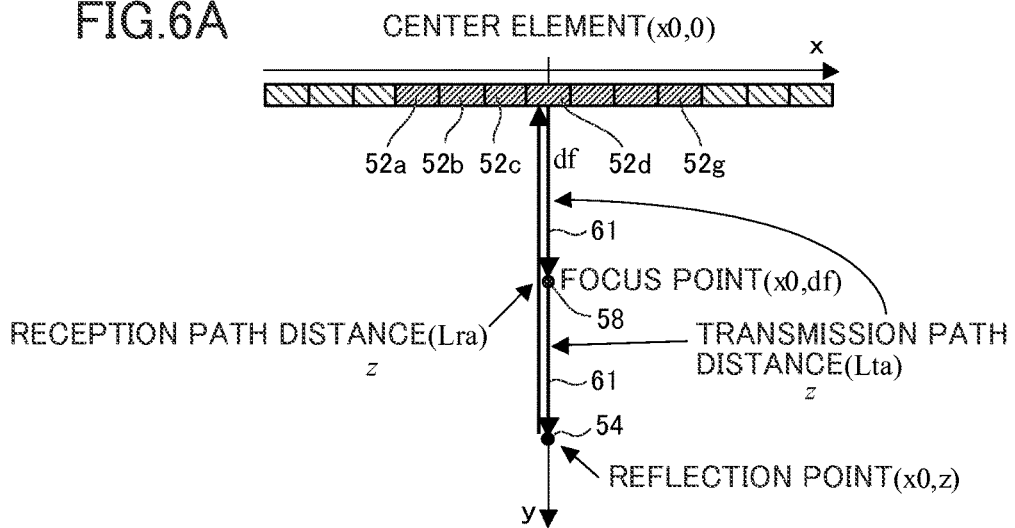
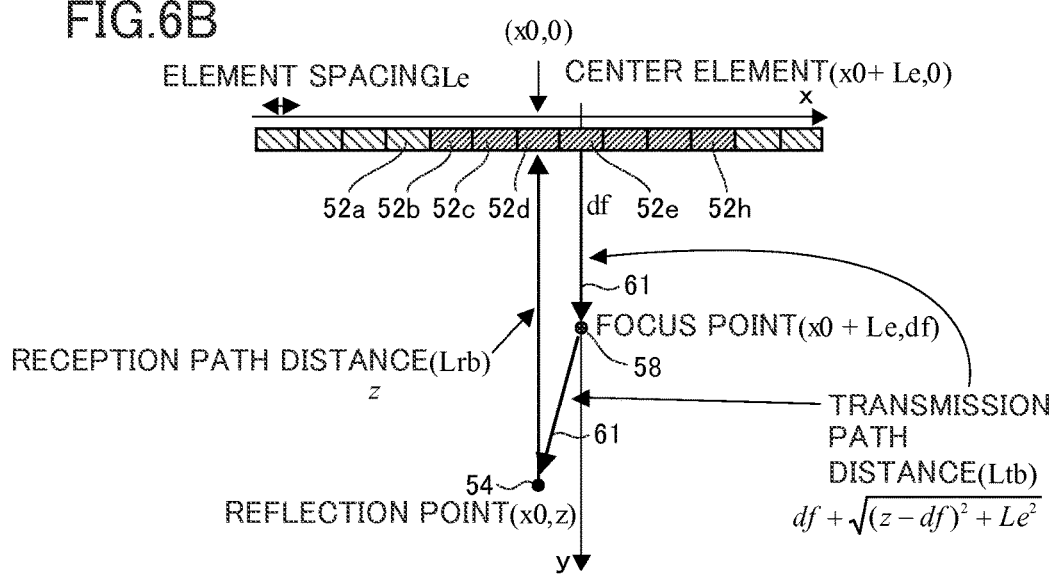
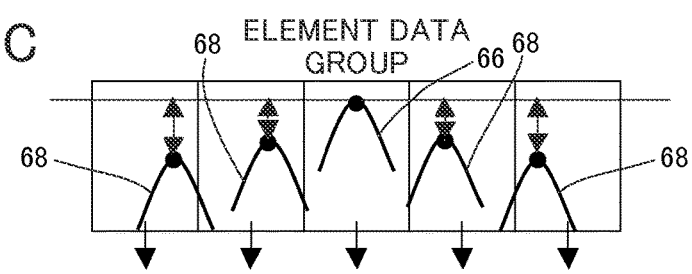
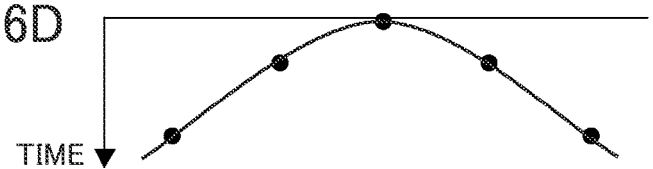

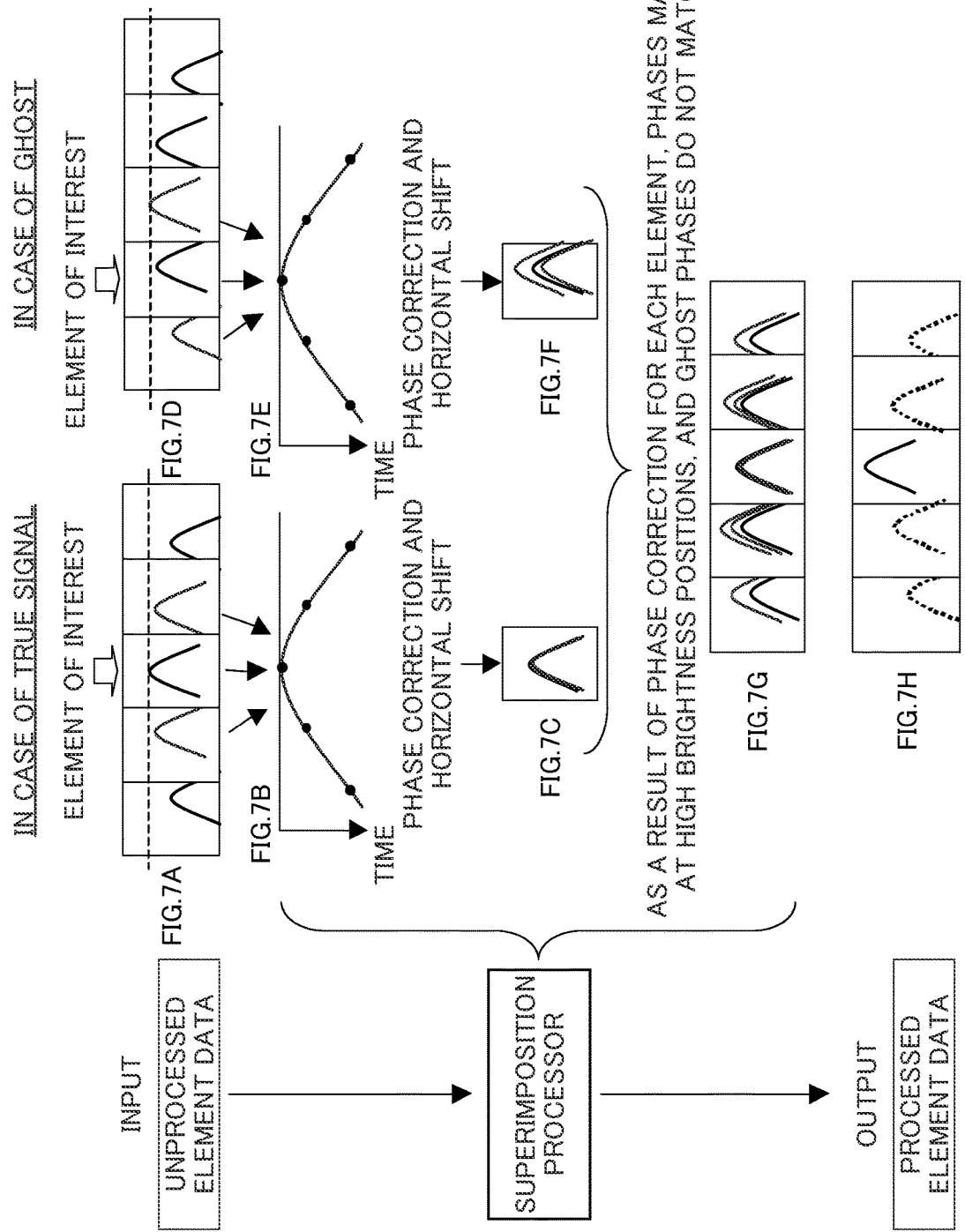

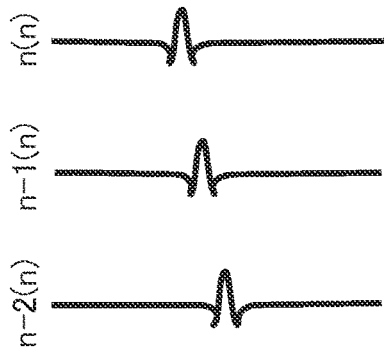
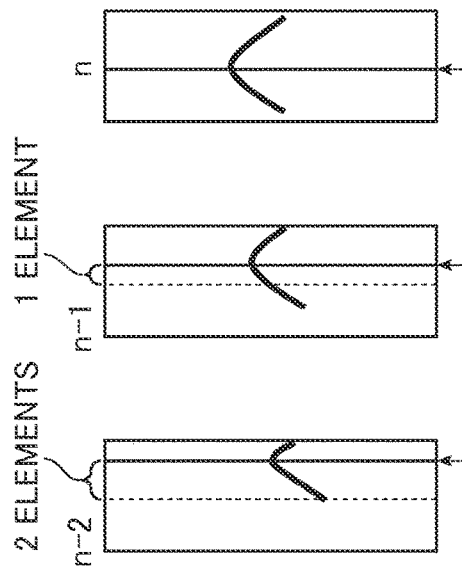

ULTRASOUND DIAGNOSTIC APPARATUS, SIGNAL PROCESSING METHOD FOR ULTRASOUND DIAGNOSTIC APPARATUS, AND RECORDING MEDIUM

CROSS-REFERENCE TO RELATED APPLICATIONS

This application is a Continuation of PCT International Application No. PCT/JP2014/052444 filed on Feb. 3, 2014, which claims priority under 35 U.S.C. § 119(a) to Japanese Patent Application No. 2013-060527 filed on Mar. 22, 2013. The above application is hereby expressly incorporated by reference, in its entirety, into the present application.

BACKGROUND OF THE INVENTION

The present invention relates to an ultrasound diagnostic apparatus for taking an image of an inspection object such as an organ in a living body by transmitting and receiving an ultrasonic beam to generate an ultrasound image used for inspection and diagnosis of the inspection object, a signal processing method, and a recording medium.

Conventionally, ultrasound diagnostic apparatuses such as ultrasound image diagnostic apparatuses using ultrasound images are put to practical use in the medical field.

Generally, this type of ultrasound diagnostic apparatus has an ultrasound probe (hereinafter, also referred to as "probe") with a plurality of built-in elements (ultrasound transducers) and an apparatus main body connected with the probe. In the ultrasound diagnostic apparatus, an ultrasonic beam is transmitted from the plurality of elements of the probe toward a subject (an inspection object) so as to form a predetermined focus point (transmission focus point), an ultrasonic echo from the subject is received by the probe, and an ultrasound image is generated by electrically processing the reception signal of the received ultrasonic echo in the apparatus main body.

Typically, in ultrasound diagnosis apparatuses, as the transmission frequency when transmitting ultrasonic beams is increased, the distance resolution is improved, but there is a greater degree of attenuation. That is, it is known that although the image quality is better as the transmission frequency is higher, there is a decrease in sensitivity.

Accordingly, the transmission frequency of the ultrasound probe is set to a transmission frequency suitable for a region (depth) to be viewed for each probe according to the purpose thereof, such as a probe for inspecting the surface of body, or a probe for inspecting an abdomen or a heart.

In addition, ultrasound probes capable of switching between transmission frequencies are also used. Using an ultrasound probe capable of switching between transmission frequencies, imaging is carried out at a high frequency when viewing a shallow region, and imaging is carried out at a low frequency when viewing a deep region. Accordingly, shallow regions can be imaged with a higher image quality and deep regions can also be appropriately imaged by suppressing decreases in sensitivity.

In the meantime, the ultrasonic beam is transmitted by the plurality of elements being driven on the basis of a predetermined transmission delay pattern so as to form a set focus point. Such an ultrasonic beam is shaped to be wide in the lateral direction. Therefore, there is a problem in that information on a reflection point located at a position shifted in the lateral direction is picked up and reproduced on the ultrasound image as a so-called ghost signal.

To solve such a problem, in formation of one ultrasound image, the ultrasound diagnostic apparatus superimposes a plurality of data (element data or reception data) obtained by each transmission according to reception times or positions of the elements to correct the data, which is so-called multi-line processing (JP 2009-240700 A). For the ghost signals, even when data is superimposed according to the reception time or the position of the elements, it is possible to eliminate the ghost signals because the ghost signals are superimposed in a shifted state and cancel each other out.

SUMMARY OF THE INVENTION

Here, in ultrasound diagnostic apparatuses that perform such multi-line processing, the transmission of the ultrasonic beams has not been performed at a transmission frequency suitable for the multi-line processing.

For example, JP 2009-240700 A discloses use of an ultrasound probe having a transducer element with a resonance frequency of 7.5 MHz; however, the use of appropriate transmission frequencies according to the processing conditions of the multi-line processing or the like has not been considered.

According to research by the present inventors, it has been found that there is a problem in that, in the multi-line processing in the ultrasound diagnostic apparatus, when the cycle of the transmission frequency is large with respect to the time difference in the reception time between data to be superimposed, the superimposition cannot be appropriately performed and the data is emphasized by overlapping even for the ghost signals and it is not possible to eliminate the ghost signals.

To solve the problems of the conventional techniques, an object of the present invention is to provide an ultrasound diagnostic apparatus, a signal processing method, and a recording medium capable of appropriately superimposing data and obtaining high quality images when correcting data by superimposing a plurality of data obtained by different instances of transmission and reception in order to generate one ultrasound image.

In order to achieve the above object, the present invention provides an ultrasound diagnostic apparatus configured to inspect an inspection object using an ultrasonic beam, the apparatus comprising:

a probe having a plurality of elements arranged therein, the probe being configured to transmit the ultrasonic beam and receive an ultrasonic echo reflected by the inspection object, and to output an analog element signal according to the received ultrasonic echo;

a transmitter configured to cause the probe to transmit the ultrasonic beam a plurality of times using at least two of the plurality of elements as transmission elements so as to form a predetermined transmission focus point;

a receiver configured to receive analog element signals output by at least two of the plurality of elements that, as reception elements, have received an ultrasonic echo corresponding to individual transmission of the ultrasonic beam and to perform a predetermined process;

an analog-to-digital converter configured to analog-to-digital convert the analog element signals processed by the receiver into first element data formed by a digital element signal;

a data processor configured to generate second element data corresponding to any one of a plurality of first element data from the plurality of first element data; and a frequency setting section configured to set a transmission frequency of the ultrasonic beam;

wherein the frequency setting section sets the transmission frequency of the ultrasonic beam according to a processing condition in the data processor; and wherein the data processor generates the second element data using the plurality of first element data obtained by the transmitter transmitting the ultrasonic beam with the transmission element at the transmission frequency set in the frequency setting section.

In the ultrasound diagnostic apparatus, the data processor preferably generates the second element data by superimposing the plurality of first element data according to the reception time at which the elements have received the ultrasonic echoes and positions of the elements.

In addition, the frequency setting section preferably sets the transmission frequency according to a time difference in reception time between the plurality of first element data to be superimposed by the data processor.

Further, the frequency setting section preferably sets a transmission frequency where a half cycle thereof is shorter than the time difference.

In addition, the frequency setting section preferably sets the transmission frequency according to at least one of a measurement depth, a position of the transmission focus point, and an arrangement spacing of the elements.

Further, the transmitter preferably changes at least one of a center element and a transmission direction of the ultrasonic beam and causes the probe to transmit the ultrasonic beam a plurality of times.

In addition, the data processor preferably generates the second element data using at least one of the plurality of first element data obtained by transmission of the ultrasonic beams for which the center elements are different to each other and the plurality of the first element data obtained by transmission of the ultrasonic beams for which the transmission directions are different to each other.

Further, the data processor preferably generates the second element data from the plurality of first element data obtained by transmission of the ultrasonic beams where transmission regions overlap.

Preferably, the ultrasound diagnostic apparatus further comprises a phasing addition section which performs phasing addition on the first element data and generates first reception data;

wherein the phasing addition section performs phasing addition on each of the plurality of first element data with a line corresponding to the same element set as the center, and generates a plurality of first reception data; and wherein the data processor generates second reception data corresponding to any one of the plurality of first reception data from the plurality of first element data.

In addition, the present invention provides a signal processing method for an ultrasound diagnostic apparatus for inspecting an inspection object using a probe having a plurality of elements arranged therein, the probe transmitting an ultrasonic beam, receiving an ultrasonic echo reflected by the inspection object, and outputting an analog element signal according to the received ultrasonic echo, the method comprising:

in the probe, a step of transmitting an ultrasonic beam a plurality of times so as to form a predetermined transmission focus point using at least two of the plurality of elements as transmission elements;

a step of receiving an ultrasonic echo corresponding to individual transmission of the ultrasonic beam with at least two of the plurality of elements as reception elements and outputting an analog element signal;

a step of analog-to-digital converting the analog element signal into first element data formed by a digital element signal;

a step of performing data processing for generating second element data corresponding to any one of a plurality of first element data from the plurality of first element data; and a step of setting a transmission frequency of the ultrasonic beam;

wherein in the step of setting the transmission frequency, the transmission frequency of the ultrasonic beam is set according to a processing condition in the step of performing data processing; and wherein, in the step of performing data processing, the second element data is generated using the plurality of first element data obtained by transmitting the ultrasonic beam at the transmission frequency set in the step of setting a transmission frequency.

Further, a non-transitory computer-readable recording medium having stored therein a program that causes a computer to execute a signal processing method for an ultrasound diagnostic apparatus for inspecting an inspection object using a probe having a plurality of elements arranged therein, the probe transmitting an ultrasonic beam, receiving an ultrasonic echo reflected by the inspection object, and outputting an analog element signal according to the received ultrasonic echo, the method comprising:

in the probe, a step of transmitting an ultrasonic beam a plurality of times so as to form a predetermined transmission focus point using at least two of the plurality of elements as transmission elements;

a step of receiving an ultrasonic echo corresponding to individual transmission of the ultrasonic beam with at least two of the plurality of elements as reception elements and outputting an analog element signal;

a step of analog-to-digital converting the analog element signal into first element data formed by a digital element signal;

a step of performing data processing for generating second element data corresponding to any one of a plurality of first element data from the plurality of first element data; and a step of setting a transmission frequency of the ultrasonic beam;

wherein in the step of setting the transmission frequency, the transmission frequency of the ultrasonic beam is set according to a processing condition in the step of performing data processing; and wherein, in the step of performing data processing, the second element data is generated using the plurality of first element data obtained by transmitting the ultrasonic beam at the transmission frequency set in the step of setting a transmission frequency.

According to the present invention, when correcting data by superimposing a plurality of data obtained by different instances of transmission, because the transmission and reception of ultrasonic waves is performed with a transmission frequency set according to the conditions of the superimposition processing, a high quality ultrasound image can be obtained because the data can be appropriately superimposed and ghost signals can be eliminated.

BRIEF DESCRIPTION OF THE DRAWINGS

FIGS. 4A and 4C are each conceptual diagrams for illustrating transmission and reception of ultrasonic waves according to an ideal ultrasonic beam, and FIGS. 4B and 4D are each conceptual diagrams illustrating element data obtained by the transmission and reception of ultrasonic waves.

FIGS. 5A and 5C are each conceptual diagrams for illustrating the transmission and reception of ultrasonic waves according to an actual ultrasonic beam, and FIGS. 5B and 5D are each conceptual diagrams illustrating element data obtained by the transmission and reception of ultrasonic waves.

FIGS. 6A and 6B are conceptual diagrams for illustrating a path of a sound wave in a case where the transmission and reception of ultrasonic waves is performed by center elements which are different to each other with respect to the same reflection point, FIG. 6C is a conceptual diagram for illustrating element data obtained by a plurality of elements, and FIG. 6D is a conceptual diagram for illustrating the element data delay time illustrated in FIG. 6C.

FIGS. 7A, 7B, and 7C are conceptual diagrams for illustrating element data for a true signal and the delay time and a state in which the element data are superimposed. FIGS. 7D, 7E, and 7F are conceptual diagrams for illustrating element data for a ghost signal and the delay time and a state in which the element data are superimposed. FIG. 7G is a conceptual diagram for illustrating a state in which element data corresponding to a plurality of elements are superimposed, and FIG. 7H is a conceptual diagram for illustrating the result of superimposing the element data in FIG. 7G.

FIGS. 16A to 16C are diagrams for illustrating phasing addition and superimposition processing in the data processor illustrated in FIG. 13.

DETAILED DESCRIPTION OF THE INVENTION

Below, detailed description will be given of the ultrasound diagnostic apparatus, the signal processing method, and the program of the present invention on the basis of a favorable first embodiment illustrated in the accompanying drawings.

Figure 1:
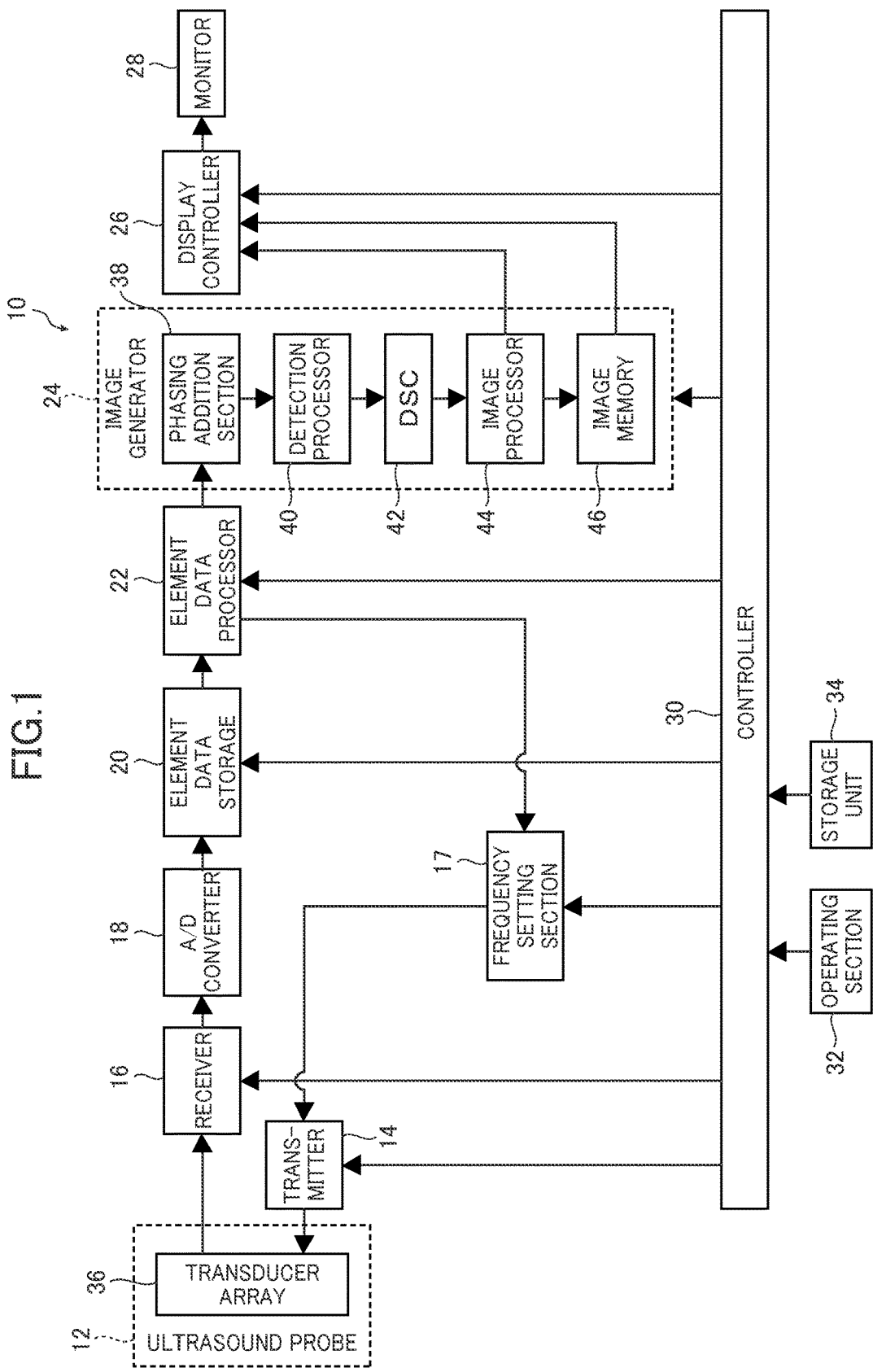
FIG. 1 is a block diagram conceptually illustrating an example of a configuration of an ultrasound diagnostic apparatus of the present invention.

FIG. 1 is a block diagram conceptually illustrating an example of the ultrasound diagnostic apparatus of the present invention which implements the signal processing method of the present invention.

As illustrated in FIG. 1, an ultrasound diagnostic apparatus 10 has an ultrasound probe 12, a transmitter 14 and a receiver 16 connected with the ultrasound probe 12, a frequency setting section 17, an analog-to-digital (A/D) converter 18, an element data storage 20, an element data processor 22, an image generator 24, a display controller 26, a monitor 28, a controller 30, an operating section 32, and a storage unit 34.

In the illustrated example, the transmitter 14, the receiver 16, the frequency setting section 17, the A/D converter 18, the element data storage 20, the element data processor 22, the image generator 24, the display controller 26, the monitor 28, the controller 30, the operating section 32, and the storage unit 34 form the apparatus main body of the ultrasound diagnostic apparatus 10.

The ultrasound probe 12 is a known ultrasound probe used in a normal ultrasound diagnostic apparatus.

The ultrasound probe 12 (hereinafter, referred to as the probe 12) has a transducer array 36 in which ultrasound transducers are one-dimensionally or two-dimensionally arranged.

When taking an ultrasound image of an inspection object (hereinafter, referred to as a subject), the ultrasound transducers each transmit ultrasonic beams to the subject in accordance with a driving signal supplied from the transmitter 14, receive ultrasonic echoes reflected by the subject, and output a reception signal according to the strength of the received ultrasonic waves.

In addition, the probe 12 is a probe capable of switching the transmission frequency of the ultrasonic waves and performs transmission of the ultrasonic beams at a transmission frequency set by the frequency setting section 17.

Each ultrasound transducer is configured by an oscillator where electrodes are formed at both ends of a piezoelectric body formed of, for example, a piezoelectric ceramic represented by lead zirconate titanate (PZT), a piezoelectric polymer represented by polyvinylidene fluoride (PVDF), a piezoelectric monocrystal represented by lead magnesium niobate-lead titanate solid solution (PMN-PT), or the like.

When a pulsed or continuous wave voltage is applied to the electrodes of the oscillator, the piezoelectric body expands and contracts according to the applied voltage, and pulsed or continuous ultrasonic waves are generated from each oscillator. In addition, the ultrasonic waves generated from the respective oscillators converge to a set focus point and are combined (that is, transmission focusing is performed on the ultrasonic waves) according to a driving delay of each of the oscillators, thereby forming an ultrasonic beam.

In addition, the oscillators expand and contract due to ultrasonic echoes reflected inside the subject being incident thereto and electric signals are generated according to the size of the expansion and contraction. The electric signals are output to the receiver 16 as the reception signals (analog element signals).

In addition, the probe 12 may be configured to be able to switch between a plurality of different predetermined transmission frequencies. For example, the probe 12 may be configured to be capable of switching between transmission frequencies of 2 MHz, 8 MHz, and 14 MHz.

The transmitter 14 has, for example, a plurality of pulse generators and supplies a driving signal (applies a driving voltage) to each of the ultrasound transducers (oscillators) of the probe 12.

The transmitter 14 performs transmission focusing for adjusting the delay amount of the driving signal (application timing of the driving voltage) and supplies the driving signal to the ultrasound transducers on the basis of a transmission delay pattern selected by the controller 30 so as to form an ultrasonic beam where the ultrasonic waves transmitted by a predetermined number (a plurality) of ultrasound transducers converge to a set focus point.

Accordingly, a desired ultrasonic beam is transmitted from the probe 12 (the transducer array 36) to the subject.

In response to a control signal from the controller 30, the receiver 16 receives reception signals output by a predetermined number (a plurality) of ultrasound transducers corresponding to a single ultrasonic beam transmission, performs predetermined processing such as amplification, and supplies the result to the A/D converter 18.

Here, the method of transmitting and receiving the ultrasonic waves in the ultrasound diagnostic apparatus 10 of the present invention is basically the same as for a known ultrasound diagnostic apparatus.

Accordingly, in a single transmission and reception of ultrasonic waves, which are the transmission of one ultrasonic beam and the reception of ultrasound echoes corresponding to this transmission, neither the number of ultrasound transducers (the number of transmission openings) which generate the ultrasonic waves nor the number of ultrasound transducers (the number of reception openings) which receive the ultrasonic waves, i.e., the receiver 16 which receives the reception signal, is limited as long as there is more than one of each. In addition, in a single transmission and reception, the number of openings may be the same or different in the transmission and the reception.

In addition, with ultrasonic beams adjacent in at least the azimuth direction (the arrangement direction of the ultrasound transducers), when transmission regions overlap, neither the number of times (number of sound rays) of the transmission and reception of the ultrasonic waves for forming one ultrasound image nor the intervals of the ultrasound transducers (center elements), that is, the density of the scanning lines/sound rays, in the center of the transmission and reception is limited. Accordingly, the transmission and reception of the ultrasonic waves may be performed with all of the ultrasound transducers corresponding to the region scanned with ultrasonic waves as the center elements, or the transmission and reception of the ultrasonic waves may be performed with ultrasound transducers at predetermined intervals, such as every two transducers or every four transducers, as the center elements.

In addition, in order to form one ultrasound image, transmission and reception is performed at a plurality of positions (lines) by sequentially moving the transmission and reception positions in the same manner as known ultrasound diagnostic apparatuses.

The frequency setting section 17 determines the transmission frequency when transmitting the ultrasonic waves according to the conditions of the superimposition processing of the element data in the element data processor 22 to be described below, specifically, according to the time difference in the reception time between the element data to be superimposed.

Detailed description will be given below of the method for determining the transmission frequency in the frequency setting section 17.

The frequency setting section 17 supplies information on the set transmission frequency to the transmitter 14.

The A/D converter 18 A/D converts the analog reception signal supplied from the receiver 16 into element data (first element data) which is a digital reception signal.

The A/D converter 18 supplies the A/D converted element data to the element data storage 20.

The element data storage 20 sequentially stores the element data supplied from the A/D converter 18. In addition, the element data storage 20 stores information (for example, the depth of the reflecting position of the ultrasonic waves, the density of the scanning lines, or a parameter indicating a visual field width) relating to the frame rate input from the controller 30 in association with each of the element data.

Preferably, the element data storage 20 stores all of the element data corresponding to at least one ultrasound image (an ultrasound image of one frame) and does not delete the element data of the ultrasound image before display or during display at least until the display of the ultrasound image is finished.

The element data processor 22 generates processed element data (second element data) corresponding to each of the element data by superimposing the element data.

Specifically, under the control of the controller 30, the element data processor 22 superimposes the element data out of the element data stored in the element data storage 20 and obtained by a predetermined number (a plurality) of ultrasonic beam transmissions for which the ultrasound transducers in the center, i.e., the elements in the center (center elements), are different and the transmission regions of the ultrasonic beams overlap, according to the time at which each of the ultrasound transducers receives the ultrasonic echoes and the positions of the ultrasound transducers, thereby generating processed element data corresponding to the element data (element data of an element of interest to be described below).

The processing in the element data processor 22 will be described in detail below.

The element data processor 22 sends the generated processed element data to the image generator 24.

The image generator 24 generates reception data (sound ray signal) from the processed element data supplied from the element data processor 22 under the control of the controller 30 and generates an ultrasound image from this reception data.

The image generator 24 has a phasing addition section 38, a detection processor 40, a digital scan converter (DSC) 42, an image processor 44, and an image memory 46.

The phasing addition section 38 performs a reception focusing process by performing matching addition on the processed element data generated by the element data processor 22, and generates reception data.

As described above, in the transducer array 36 of the probe 12, a plurality of elements (ultrasound transducers) is one-dimensionally or two-dimensionally arranged. Accordingly, the distance to one reflection point in the subject is different for each ultrasound transducer. Therefore, even with ultrasonic echoes reflected at the same reflection point, the time for the ultrasonic echoes to arrive at each of the ultrasound transducers is different. The phasing addition section 38 performs a digital reception focusing process and generates reception data by performing matching addition on the processed element data to which a delay time is applied by delaying each signal of the processed element data by an amount equivalent to the difference in the arrival time (delay time) of ultrasonic echoes for each of the ultrasound transducers, according to a reception delay pattern selected by the controller 30.

The phasing addition section 38 supplies the generated reception data to the detection processor 40.

Figure 2:
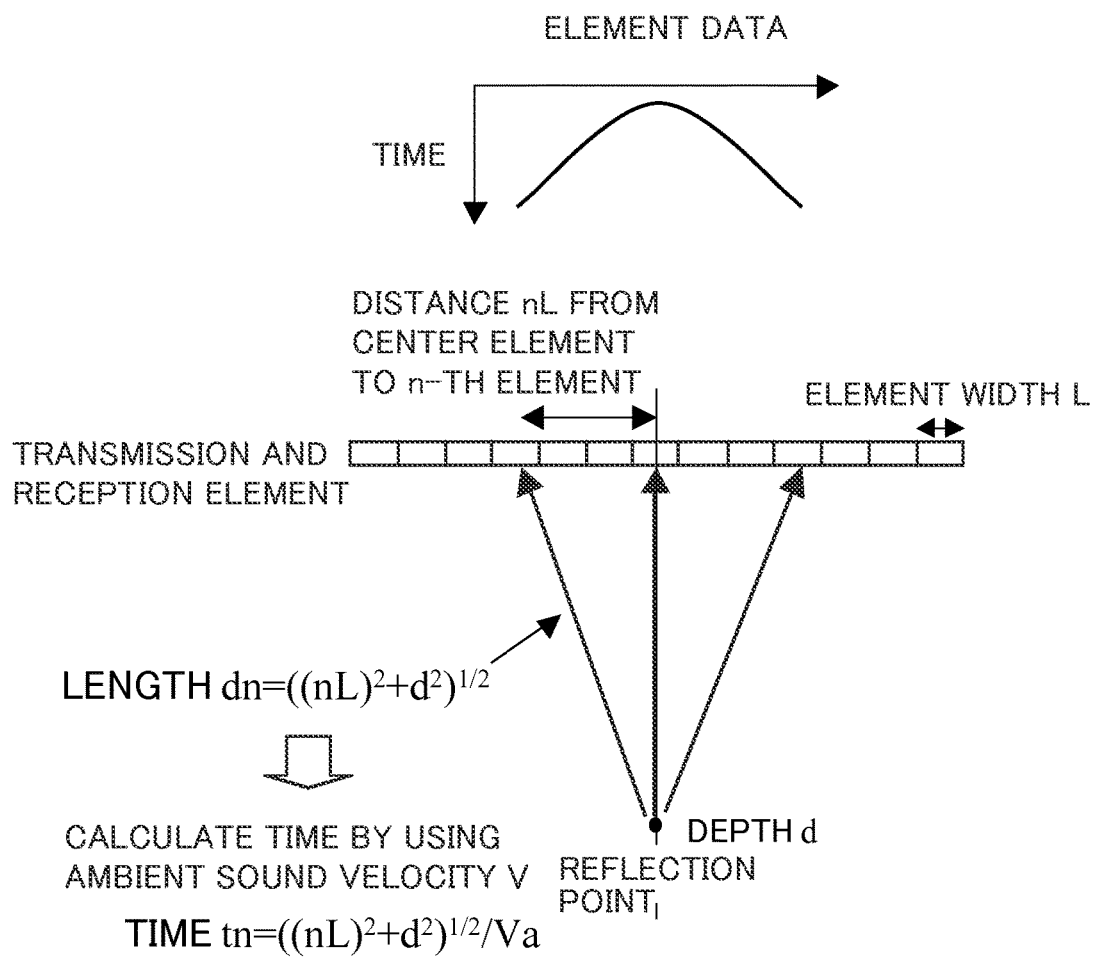
FIG. 2 is a conceptual diagram for describing an example of a reception focusing process in the ultrasound diagnostic apparatus depicted in FIG. 1.

FIG. 2 illustrates an example of the reception focusing process.

Here, FIG. 2 illustrates a case of a linear probe where the plurality of ultrasound transducers of the probe 12 is arranged in a row in the left and right direction in the diagram. However, the concept may be similarly applied even in the case of a convex probe where only the probe shape is different.

When the width of each of the ultrasound transducers in the azimuth direction is taken to be L, the distance up to the n-th ultrasound transducer from the ultrasound transducer in the center of the azimuth direction toward the end section is nL.

As illustrated in the same diagram, when the reflection point of the ultrasonic waves is taken to be at a position at a distance (depth) d, which is perpendicular to the arrangement direction, from the center ultrasound transducer, the distance (length) d, between the n-th ultrasound transducer and the reflection point is calculated using the formula (1).

$$d_n = ((nL)^2 + d^2)^{1/2} \quad (1)$$

Accordingly, using the ultrasound sound velocity (ambient sound velocity) Va in the subject, the time $t_n$ for the ultrasonic echoes to reach (be received by) the n-th ultrasound transducer from the reflection point is calculated using Formula (2).

$$t_n = d_n/Va = ((nL)^2 + d^2)^{1/2}/Va \quad (2)$$

As described above, the distance between the ultrasound transducers and the reflection point is different for each ultrasound transducer. Therefore, in the case of this example, as shown in the graph at the top of the same diagram, the arrival time to of the ultrasonic echoes is longer for the ultrasound transducers toward the end section sides in the arrangement direction.

Specifically, when the time until the ultrasonic waves are received by the center ultrasound transducer from the reflection point is taken to be $t_1$, the ultrasonic waves received by the n-th ultrasound transducer are delayed by the time $\Delta t = t_n - t_1$ with respect to the ultrasonic waves received by the center ultrasound transducer. In the present example, the delay time $\Delta t$ is a reception delay pattern.

The phasing addition section 38 performs phasing addition using a delay time represented by the time $\Delta t$ described above, performs the reception focusing process, and generates reception data for signals corresponding to each of the ultrasound transducers.

After performing correction of the attenuation due to the distance according to the depth of the reflection position of the ultrasonic waves on the reception data generated by the phasing addition section 38, the detection processor 40 generates B mode image data formed by tomographic image information (brightness image information) in the subject by performing envelope detection processing.

The digital scan converter (DSC) 42 converts (raster converts) the B mode image data generated by the detection processor 40 into image data corresponding to a normal television signal scanning system.

The image processor 44 performs various necessary image processing such as gradation processing on the B mode image data input from the DSC 42 to create B mode image data for display. The image processor 44 outputs the image processed B mode image data to the display controller 26 for display and/or stores the image processed B mode image data in the image memory 46.

The image memory 46 is a known storage (a storage medium) which stores the B mode image data processed by the image processor 44. The B mode image data stored in the image memory 46 is read out by the display controller 26 for display on the monitor 28 as necessary.

The display controller 26 uses the B mode image data on which the predetermined image processing is performed by the image processor 44 to display an ultrasound image on the monitor 28.

The monitor 28 includes a display device such as an LCD, and displays an ultrasound image under the control of the display controller 26.

The controller 30 controls each section of the ultrasound diagnostic apparatus 10 on the basis of instructions input from the operating section 32 by an operator.

In addition, the controller 30 supplies various types of information input by the operator using the operating section 32 to necessary units. For example, in a case where information necessary for the transmission frequency setting which is used by the frequency setting section 17, information necessary for the delay time calculation which is used by the element data processor 22 and the phasing addition section 38 of the image generator 24, and information necessary for the element data processing in the element data processor 22 are input to the operating section 32, the information is supplied to each section such as the transmitter 14, the receiver 16, the frequency setting section 17, the element data storage 20, the element data processor 22, the image generator 24, the display controller 26, and the like as necessary.

The operating section 32 is a section for the operator to make input operations, and can be constituted by a keyboard, a mouse, a trackball, a touch panel, or the like.

In addition, the operating section 32 is provided with an input function for the operator to input various types of information as necessary. For example, the operating section 32 is provided with an input function for inputting information on the probe 12 (the ultrasound transducer); information relating to the generation of the processed element data such as the transmission opening and the reception opening in the probe 12 (the transducer array 36), the number of element data to be superimposed, or the generation method; the focus point position of the ultrasonic beam; and the like.

The above are input, for example, by selecting the photograph site (the examination site), selecting the image quality, selecting the depth of the ultrasound image to be photographed, or the like.

The storage unit 34 stores information necessary for the controller 30 to operate and control the ultrasound diagnostic apparatus such as information relating to an operation program for the controller 30 to execute control of each section of the ultrasound diagnostic apparatus 10, the transmission delay pattern and the reception delay pattern, and the generation of processed element data; information on the probe 12 input from the operating section 32; information on the transmission opening, the reception opening, and the focus point position.

In the storage unit 34, it is possible to use a known recording medium such as a hard disk, a flexible disk, an MO, an MT, a RAM, a CD-ROM, or a DVD-ROM.

Here, in the ultrasound diagnostic apparatus 10, the frequency setting section 17, the element data processor 22, the phasing addition section 38, the detection processor 40, the DSC 42, the image processor 44, the display controller 26, and the like are configured by a CPU and an operation program for causing the CPU to perform various types of processes. However, in the present invention, these units may be configured by a digital circuit.

As described above, the element data processor 22 generates processed element data by superimposing element data out of the element data (the unprocessed element data) stored in the element data storage 20 and obtained by a predetermined number (a plurality) of ultrasonic beam transmissions, for which the center ultrasound transducers (the center elements) are different and the transmission regions of the ultrasonic beams overlap, according to the time of being received by each ultrasound transducer and the position of the ultrasound transducers.

Here, in the following description, the ultrasound transducers are also referred to simply as "elements".

Figure 3:
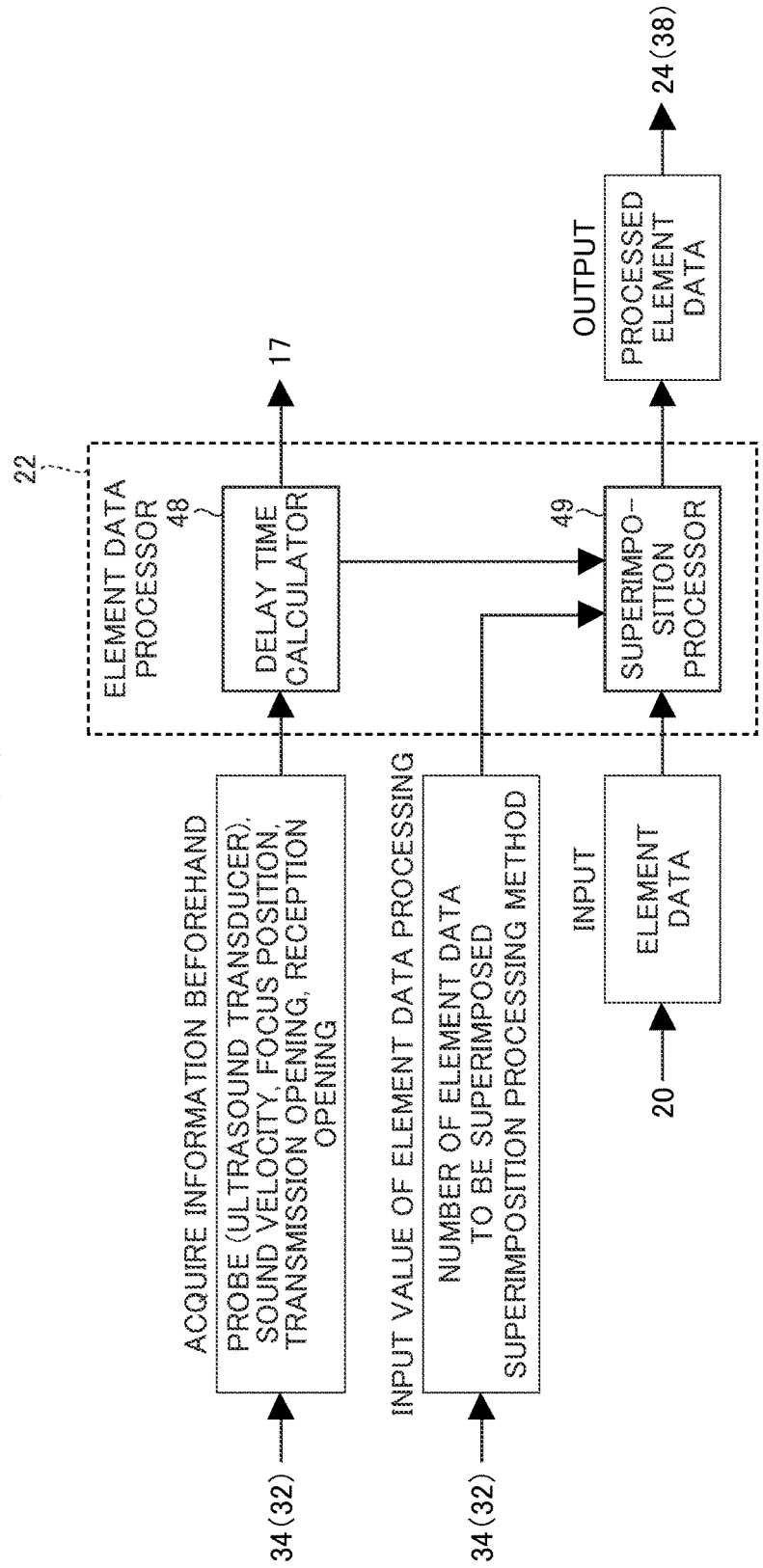
FIG. 3 is a block diagram conceptually illustrating an example of a configuration of an element data processor of the ultrasound diagnostic apparatus depicted in FIG. 1.

FIG. 3 is a block diagram conceptually illustrating the configuration of the element data processor 22.

As illustrated in FIG. 3, the element data processor 22 has a delay time calculator 48, and a superimposition processor 49.

The delay time calculator 48 acquires in advance information, which is input from the operating section 32 or input from the operating section 32 and stored in the storage unit 34, on the probe 12 (ultrasound transducer (element)), the focus point position of the ultrasonic beam, the sampling point position (output position of the element data), the transmission openings and reception openings of the probe 12, and the like.

In addition, the delay time calculator 48 calculates the delay time of the ultrasonic echoes received by the elements of the reception openings, that is, the element data, on the basis of the geometric positions of the elements of the transmission openings which oscillate the ultrasonic waves in order to transmit (generate) the ultrasonic beams and the elements of the reception openings which receive the ultrasonic echoes from the subject.

Here, before the transmission and reception of ultrasonic waves is performed, the delay time calculator 48 calculates and supplies the delay time to the frequency setting section 17.

The delay time calculator 48 supplies information on the calculated delay time to the superimposition processor 49 and the frequency setting section 17.

The superimposition processor 49 reads out element data (element data for which the center elements are different and which is obtained by ultrasonic beams for which the transmission regions are overlapped (two or more element data generated for each of two or more target regions)) to be superimposed from the element data stored in the element data storage 20 on the basis of information relating to the element data processing such as the number of element data to be superimposed or the superimposition processing method which is input from the operating section 32 or input from the operating section 32 and stored in the storage unit 34.

Furthermore, on the basis of the delay time corresponding to each of the element data calculated by the delay time calculator 48, the superimposition processor 49 generates processed element data by matching two or more element data according to the reception time, that is, matching the time, and by matching and superimposing the absolute positions of the elements of the receiving probes.

Below, detailed description will be given of the processing of the element data performed by the element data processor 22.

Firstly, description will be given of a relationship between ultrasonic beams from the transmission elements and element data obtained by the reception elements in a case where, in the ultrasound probe 12, the ultrasonic beams are transmitted to the subject from the transmission opening, that is, the element (hereinafter, simply referred to as the transmission element) which sends out the ultrasonic waves in order to transmit the ultrasonic beams, and the element data is obtained by receiving the ultrasonic echoes generated by interaction with the subject in the reception opening, that is, in the element (hereinafter, simply referred to as the reception element) which receives the ultrasonic echoes.

As an example, as illustrated in FIG. 4A, the ultrasonic beams are transmitted with three elements 52*c* to 52*e* as transmission elements and the ultrasonic echoes are received with seven elements 52*a* to 52*g* as reception elements. Next, as illustrated in FIG. 4C, the ultrasonic beams are transmitted with three elements 52*d* to 52*f* as transmission elements by moving (hereinafter, also referred to as shifting) the elements by one element in the azimuth direction and each of the element data is acquired by receiving the ultrasonic echoes with seven elements 52*b* to 52*h* as the reception elements.

That is, the center element (the element in the center) is the element 52*d* in the example illustrated in FIG. 4A and the center element is the element 52*e* in the example illustrated in FIG. 4C.

Now, an ideal case will be considered in which ultrasonic beams 56 transmitted to the inspection object region including a reflection point 54 are converged to a focus point 58 and narrowed to the element spacing or less.

As illustrated in FIG. 4A, when ultrasonic beams 56 are transmitted from the elements 52*c* to 52*e* which are transmission elements with the element 52*d* directly above (on a straight line linking the reflection point and the focus point) the reflection point 54 as the center element and the element data is acquired by receiving the ultrasonic echoes in the elements 52*a* to 52*g* which are the reception elements, the focus point 58 of the ultrasonic beam 56 is on a straight line linking the element 52*d* which is the center element and the reflection point 54. In such a case, because the ultrasonic beam 56 is transmitted up to the reflection point 54, the ultrasonic echoes reflected by the reflection point 54 are generated.

The ultrasonic echoes from the reflection point 54 are received in the elements 52*a* to 52*g* which are the reception elements after passing through a reception path 60 extending at a predetermined angle and the element data 62 as illustrated in FIG. 4B is obtained by the elements 52*a* to 52*g*. Here, in FIG. 4B, the vertical axis represents the time and the horizontal axis represents the position (the position of the elements) in the azimuth direction corresponding to FIG. 4A (the same applies to FIG. 4D).

In contrast, as illustrated in FIG. 4C, in a case where the center element is shifted by one element, the element 52*e* next to the element 52*d* directly above the reflection point 54 becomes the center element.

The ultrasonic beam 56 is transmitted from the elements 52*d* to 52*f* which are transmission elements with the element 52*e* as the center element and the ultrasonic echoes are received in the elements 52*b* to 52*h* which are the reception elements. At this time, in the same manner, when the ultrasonic beam 56 is ideal, the reflection point 54 is not present in the transmission direction of the ultrasonic beam 56, that is, on a straight line linking the center element 52*e* and the focus point 58. Accordingly, the ultrasonic beam 56 is not transmitted to the reflection point 54.

Therefore, because ultrasonic echoes reflected by the reflection point 54 are not generated and the elements 52*b* to 52*h*, which are reception elements, do not receive ultrasonic echoes from the reflection point 54, the element data does not include a reflected signal from the reflection point as illustrated in FIG. 4D (the signal strength of the element data is 0).

However, because the actual ultrasonic beam is diffused after converging to the focus point 58 as in the ultrasonic beam 64 illustrated in FIG. 5A and FIG. 5C, the actual ultrasonic beam has a width wider than the element interval.

Here, similar to FIG. 4A, in a case where the ultrasonic beam 64 is transmitted with the elements 52*c* to 52*e* as the transmission elements and the element 52*d* directly above the reflection point 54 as the center element as in FIG. 5A, even when the ultrasonic beam 64 is wide, the focus point 58 is on a straight line linking the element 52*d* and the reflection point 54. Accordingly, the ultrasonic beam 64 is reflected at the reflection point 54 and ultrasonic echoes are generated.

As a result, in the same manner as the case of FIG. 4A, the ultrasonic echoes from the reflection point 54 are received in the elements 52*a* to 52*g* which are the reception elements after passing through the reception path 60 which widens at a predetermined angle, and, similarly, true element data 66 as illustrated in FIG. 5B is obtained.

Next, similar to FIG. 4C, as illustrated in FIG. 5C, the ultrasonic beam 56 is transmitted after shifting the center element by one element, setting the adjacent element 52*e* as the center element, and setting the elements 52*d* to 52*f* as the transmission elements, and the ultrasonic echoes are received with the elements 52*b* to 52*h* as the reception elements. Even in such a case, because the ultrasonic beam 64 is wide, the ultrasonic beam 64 is transmitted to (arrives at) the reflection point 54 even when the reflection point 54 is not present in the transmission direction of the ultrasonic waves, that is, on a straight line linking the element 52*e* which is the center element and the focus point 58.

Therefore, ultrasonic echoes which are not inherently present or so-called ghost reflected echoes are generated in the transmission direction of the ultrasonic beam from the reflection point 54. The ghost reflected echoes from the reflection point 54 are received in the elements 52*b* to 52*h* which are reception elements after passing through the reception path 60 which widens at a predetermined angle as illustrated in FIG. 5C. As a result, ghost element data 68 as illustrated in FIG. 5D is obtained by the elements 52*b* to 52*h*.

In this manner, the ghost element data 68 is a cause of the precision of the ultrasound image generated from the element data decreasing.

The element data processor 22 calculates the delay time corresponding to the element data in the delay time calculator 48, and generates processed element data constituted by high precision element data for which the ghost signals are attenuated by the true element data being emphasized by the superimposition processor 49 superimposing two or more of element data according to the delay time and the absolute position of the elements.

As described above, the delay time calculator 48 calculates the delay time of the element data received in each of the reception elements (reception openings).

That is, the propagation distance of the ultrasonic beam 64 illustrated in FIG. 5C is the sum of the transmission path where the ultrasonic beam 64 reaches the reflection point 54 from the element 52*e* which is the center element via the focus point 58 and the reception path where the ghost reflected echoes from the reflection point 54 reach each of the elements 52*b* to 52*h* which are the reception elements.

The propagation distance of the ultrasonic beam 64 illustrated in FIG. 5C is longer than the propagation distance of the ultrasonic beam 64 illustrated in FIG. 5A, that is, the sum of the transmission path where the ultrasonic beam 64 reaches the reflection point 54 from the center element 52*d* via the focus point 58 and the reception path where the true ultrasonic echoes from the reflection point 54 reach the elements 52*a* to 52*g* which are the reception elements.

Therefore, the ghost element data 68 as illustrated in FIG. 5D is delayed with respect to the true element data 66 as illustrated in FIG. 5B.

In the delay time calculator 48 of the element data processor 22, the time difference between the true element data and the ghost element data, that is, the delay time is calculated from the sound velocity, the transmission elements, the focus point of the ultrasonic beam, the reflection point of the subject, and the geometric arrangement of the reception elements.

Accordingly, in the calculation of the delay time, information such as the shape of the probe 12 (the element spacing, the probe being linear, convex, or the like), the sound velocity, the position of the focus point, the transmission opening, and the reception opening is necessary. In the delay time calculator 48, the information input by the operating section 32 or stored in the storage unit 34 is acquired to calculate the delay time. Here, a fixed value (for example, 1540 m/sec) may be used as the sound velocity. Alternatively, in a case where there is a sound velocity calculator, a sound velocity (ambient sound velocity) calculated by the sound velocity calculator may be used as the sound velocity, or an operator may input the sound velocity.

It is possible for the delay time to be calculated from the difference in the propagation time calculated according to the sound velocity and the total length (propagation distance) of the transmission path of the ultrasonic beam from the transmission element to the reflection point via the focus point and the reception path of true reflected ultrasonic echoes or the ghost reflected signal from the reflection point up to the reception elements, which is calculated from the geometric arrangement of, for example, the transmission elements, the focus point of the ultrasonic beam, the reflection point of the subject, and the reception elements.

In the present invention, for example, as illustrated in FIG. 6A and FIG. 63, it is possible to determine the length of the transmission path and the reception path of the ultrasonic beam in the case of the true ultrasonic echoes and the ghost reflected echoes. Here, in FIGS. 6A and 6B, the x direction is the azimuth direction and the y direction is the depth direction.

In addition, in FIG. 6A, the transmission and reception of the ultrasonic waves is performed in the same manner as in FIG. 5A and, in FIG. 6B, the transmission and reception of the ultrasonic waves is performed in the same manner as in FIG. 5C.

In the case of the true ultrasonic echoes, as illustrated in FIG. 6A (FIG. SA), the element 52*d* which is the center element, the focus point 58, and the reflection point 54 are positioned on a straight line (the positions are matched in the azimuth direction). That is, the focus point 58 and the reflection point 54 are positioned directly below the center element 52*d*.

Accordingly, when the position of the element 52*d* which is the center element is taken to be coordinates (x0, 0) which are two dimensional x-y coordinates, the x coordinate of the focus point 58 and the reflection point 54 is also "x0". Below, the position of the focus point 58 in the transmission is taken to be coordinates (x0, df), the position of the reflection point 54 is taken to be coordinates (x0, z), and the element spacing is taken to be Le.

At this time, it is possible for the length (transmission path distance) Lta of a transmission path 61 of the ultrasonic beam from the element 52d which is the center element to the reflection point 54 via the focus point 58 and the length (the reception path distance) Lra of the reception path 60 of the true reflected ultrasonic echoes from the reflection point 54 to the element 52d to be calculated using Lta=Lra=z.

Accordingly, in the case of the true ultrasonic echoes, the propagation distance Lua of the ultrasonic echoes is Lua=Lta+Lra=2z.

Next, as illustrated in FIG. 6B, by shifting (shifting in the direction to the right in the diagram) the transmission element and the reception element by one element in the x direction (the azimuth direction), transmission and reception are performed with the element 52e as the center element. As illustrated in FIG. 5C, in this case, the echoes reflected at the reflection point 54 are the ghost reflected echoes.

The reflection point 54 is positioned directly below (at the same position in the azimuth direction) the element 52d. Accordingly, as illustrated in FIG. 6B, the positions of the element 52e which is the center element and the reflection point 54 in the x direction are shifted in the x direction by one element, that is, by Le in the transmission and the reception.

Because the coordinates of the element 52d whose position matches the reflection point 54 in the x direction are (x0, 0), the coordinates of the element 52e which is the center element become (x0+Le, 0) and the coordinates of the focus point 58 in the transmission become (x0+Le, df). Here, as described above, the coordinates of the reflection point 54 are (x0, z).

Accordingly, the length (transmission path distance) Ltb of the transmission path 61 of the ultrasonic beams arriving at the reflection point 54 from the element 52e, which is the center element, through the focus point 58 can be calculated using Ltb=df+$\sqrt{\{(z-df)^2+Le^2\}}$. On the other hand, the length (the reception path distance) Lrb of the reception path 60 of the ghost reflected signal from the reflection point 54 to the element 52d directly below (at the same position in the x direction=azimuth direction) can be calculated using Lrb=z.

Accordingly, the propagation distance Lub of the ultrasonic waves in the case of ghost reflected echoes is Lub=Ltb+Lrb=df+$\sqrt{\{(z-df)^2+Le^2\}}$+z.

In this manner, a value where the propagation distance Lua of the ultrasonic waves which is the total of the distance Lta of the transmission path 61 and the distance Lra of the reception path 60 determined by the geometric arrangement illustrated in FIG. 6A is divided by the sound velocity is the propagation time of the true ultrasonic echoes. In addition, a value where the propagation distance Lub of the ultrasonic waves which is the total of the distance Ltb of the transmission path 61 and the distance Lrb of the reception path 60 determined by the geometric arrangement illustrated in FIG. 6B is divided by the sound velocity is the propagation time of the ghost reflected echoes.

The delay time is determined from the difference between the propagation time of the true ultrasonic echoes when the x coordinates of the reflection point 54 and the center element are matched and the propagation time of the ghost reflected echoes when the x coordinates of the reflection point 54 and the center element are shifted by a single element interval at a time.

Here, the geometric model of FIG. 6A and FIG. 6B is a model where the transmission path 61 goes via the focus point 58; however, the present invention is not limited thereto, and, for example, may be a path arriving directly at the reflection point 54 without going via the focus point 58.

In addition, the geometric model of FIG. 6A and FIG. 6B is for the case of a linear probe; however, without being limited thereto, it is possible to perform the geometric calculation in the same manner from the shape of the probe even with other probes.

For example, in the case of a convex probe, it is possible to perform the calculation in the same manner by setting the geometric model using the radius of the probe and angle of the element interval.

In addition, in the case of a steer transmission, it is possible to calculate the delay time of the true element data and the ghost element data of the surroundings thereof from the positional relationship between the transmission elements and the reflection points using a geometric model taking information such as the transmission angle into consideration.

Furthermore, without being limited to a method of calculating the delay time according to a geometric model, by determining the delay time for every measuring condition from the measuring results of measuring the high brightness reflection point in accordance with the measuring conditions of the apparatus in advance and storing the delay times in the apparatus, the delay time for the same measuring conditions may be read out.

FIG. 6C illustrates the true element data 66 and the ghost element data 68.

In FIG. 6C, the center in the azimuth direction is the true element data 66, that is, element data (element data where the element 52d is taken to be the center element in the example in the diagram) obtained by transmission and reception where the positions of the center element and the reflection point 54 match in the x direction. In addition, both sides of the center are ghost element data, that is, element data (element data where the element data 52c or the element 52e is taken to be the center element in the example in the diagram) obtained by transmission and reception where the positions of the center element and the reflection point 54 do not match in the x direction.

In addition, FIG. 6D illustrates an example of the delay time of the ghost element data 68 with respect to the true element data 66 obtained by the geometric calculation described above. Centering on the true element data 66, the element data 68 of the ghost signal indicates that the time is symmetrically delayed in the x direction, that is, the azimuth direction.

Here, in this manner, it is also possible for the delay time calculated in the delay time calculator 48 of the element data processor 22 to be used in the delay correction in the phasing addition section 38.

As will be described in detail below, in the present invention, by superimposing element data, which is obtained by the transmission of the ultrasonic beam where at least a portion of the ultrasonic beam overlaps and for which the center element is different, on element data, which is obtained by the transmission (the transmission and reception of the element of interest) of an ultrasonic beam where a certain element of interest is the center element, by matching the reception time of the ultrasonic echoes and the position of the elements, the processed element data (second element data) of the element of interest is generated (the element data of the element of interest is rebuilt).

In FIG. 6A, the reflection point 54 indicates the position (the output position of the element data) of a certain sampling point positioned directly below the element of interest (at the same position in the azimuth direction or on a straight line linking the element of interest and the focus point). In the present invention, the transmission and reception path to the sampling point in the transmission and reception of the element of interest is regarded as the transmission and reception path of the true element data and the transmission and reception path to the same sampling point in the transmission and reception (the transmission and reception from the surrounding elements) of the ultrasonic waves where the center element is different is regarded as the ghost transmission and reception path. The superimposition is performed by calculating the delay time from the difference between both transmission paths and matching the time of the element data using the delay time. In other words, the delay time is calculated and the superimposition of the element data is performed assuming that element data obtained by the transmission and reception of the element of interest is the true element data and element data obtained by the transmission and reception where the center element is different is the ghost element data.

In the present invention, the superimposition of the element data is performed by calculating the delay time with the same concept corresponding to all of the sampling points (the output position of all the element data) and the processed element data of each of the elements is generated.

Here, in fact, even when the positions of the sampling points (reflection points) are shifted in the azimuth direction (the x direction), the length of the reception path (the reception path distance Lrb) does not change. Accordingly, in relation to each of the elements of interest, the calculation of the delay times of the element data according to transmission and reception for which the center elements are different may be performed for every sampling point in the depth direction (the y direction).

In addition, it is not necessary to know which element data is the true element data in the superimposition processing. That is, although described in detail with reference to FIGS. 7A to 7H below, in the superimposition processing, the element data of the element of interest is automatically emphasized and remains when the element data is the true element data and the element data is canceled when the element data is ghost element data. That is, in a case where the element data of the element of interest is the true element data, the signal is emphasized by matching the process according to the delay time and, in a case where the element data of the element of interest is the ghost element data, the signal is canceled without matching the process according to the delay time.

Next, in the superimposition processor 49 of the element data processor 22 of the present invention, the superimposition processing of the element data is performed using the delay time calculated in the delay time calculator 48 in this manner.

Here, in the superimposition processing in the superimposition processor 49, information on the superimposition processing method and the number of superimposition element data at the time of the superimposition is necessary; however, this information may be input using the operating section 32 in advance, or may be stored in the storage unit 34 in advance.

FIGS. 7A to 7H illustrate an example of superimposition processing performed by the superimposition processor 49. Here, the example illustrated in FIGS. 7A to 7H is of a case where the number of element data is five and the number of superimposed element data is three.

FIG. 7A illustrates five pieces of element data obtained by performing the transmission and reception of the ultrasonic waves five times are lined up side by side. In addition, FIG. 7A represents a state where ultrasonic echoes are received after the ultrasonic beams are transmitted for each element data. The horizontal axis of each element data represents a reception element and displays the center element in the center in the transmission and reception of the ultrasonic beam in each of the element data. The vertical axis represents the reception time. In this example, transmission and reception of the ultrasonic waves is performed five times by shifting the center element by one element at a time, for example, in the above-described elements 52b to 52f or the like.

FIG. 7A illustrates a state in which one reflection point is present only directly below the center element in the center element data. That is, out of the five element data, the true ultrasonic echoes are received in the element data in the middle from the reflection point in the transmission and reception of the ultrasonic waves. That is, the element data in the middle is the true element data.

Regarding the two element data on both sides other than the element data in the middle, the reflection point is not present directly below the center element in the transmission and reception of the ultrasonic waves. However, due to the ultrasonic beam hitting the reflection point which is present directly below the transmission element of the element data in the middle according to the spread of the transmitted ultrasonic beam, the generated reflected echo element data, that is, the ghost element data is reflected.

The further the ghost element data is separated from the true element data, the longer the propagation time of the ultrasonic waves up to the reflection point, thus the reception time for the ghost element data is longer than that for the true element data. In addition, the position of the reception element where the ultrasonic echoes from the reflection point are first received is directly above the reflection point (an element whose position in the azimuth direction matches the reflection point).

Here, the horizontal axes of each of the element data in FIG. 7A set the center element during the transmission of the ultrasonic beam in the center. Accordingly, in the examples illustrated in FIG. 7A, because transmission is carried out by shifting the center element by one element for each of the element data, the absolute position of the elements in the azimuth direction in each element data is shifted by one element at a time. In other words, in the element data in the middle, the reception element which first receives the reflected signal from the reflection point is the center element; however, in both adjacent element data, the reception element is shifted by one element from the element data in the middle, the element data on the right side is shifted by one element to the left, and the element data on the left side is shifted one element to the right. Furthermore, the element data on both ends is shifted by two elements from the element data in the middle, the element data at the right end is shifted by two elements to the left, and the element data at the left end is shifted by two elements to the right. In this manner, not only is the reception time longer for the ghost signals than that for the true signal, but shifting is also generated with respect to the direction of the reception elements.

FIG. 7B illustrates an example of the delay time of the reception time with respect to the element data in the middle of the five element data illustrated in FIG. 7A.

In the superimposition processor 49, in a case where the center element of the element data in the middle is set as the element data of the element of interest, the delay time correction is performed according to the number of element data to be superimposed (three elements in the example in the diagram) centering on the element data of the element of interest using the delay time illustrated in FIG. 7B. Also, by shifting each element data by one element in the azimuth direction at both sides in the example in the diagram according to the difference of the element position on the element of interest (difference with the position of the center element), that is, by matching the phases, unprocessed element data for three elements are superimposed and determined as one superimposition processed element data for the element of interest.

That is, in the present example, the processed element data of the element data of the element of interest is generated by superimposing the element data (hereinafter, also referred to as the element data of the adjacent element) obtained by transmission and reception of the ultrasonic waves where the element adjacent to the element of interest is the center element on the element data (hereinafter, also referred to as element data of the element of interest) obtained by the transmission and reception of the ultrasonic waves where the element of interest is the center element.

The superimposition processed element data of the element of interest obtained in this manner is illustrated in FIG. 7C.

As described above, the element data of the element of interest illustrated in FIG. 7A is true element data in which the reflection point is present directly below the center element (that is, the element of interest). In addition, the element data obtained by the transmission and reception where an element adjacent to the element of interest is the center element is also ultrasonic echo data where the ultrasonic waves are incident on the reflection point and reflected.

Accordingly, when performing the phase matching by performing delay time correction and azimuth direction shifting on the element data of the elements adjacent at both sides of the element data of the element of interest, the element data of the adjacent element and the element data of the element of interest overlap at a high brightness position because the phases match as illustrated in FIG. 7C. Therefore, for example, when the element data are added, the element data value indicates a large value (high brightness value). For instance, the element data indicates an emphasized value (high brightness value) even when an average value is determined by averaging.

In contrast, FIG. 7D illustrates an example of a case with the same element data as FIG. 7A; however, the center element of the element data adjacent to the left of the element data in the middle is the element of interest. That is, this example shows a case of the transmission and reception of ultrasonic waves where an element for which the reflection point is not present directly below is the center element, in which the center element is the element of interest. Accordingly, the element data where the element is the center element is ghost element data.

FIG. 7E is the same as FIG. 7B and illustrates an example of the delay time of the reception time with respect to the element data of the element of interest of the five element data illustrated in FIG. 7A. That is, because FIG. 7A and FIG. 7D are of the same element data, the delay time of the reception time with respect to the element data in the middle of the five element data illustrated in FIG. 7D is also the same.

In the superimposition processor 49, the delay time correction is performed according to the number of element data to be superimposed (three elements in the example in the diagram) centering on the element data of the element of interest using the delay time illustrated in FIG. 7E (that is, the same as FIG. 7B). Also, by shifting each element data by one element in the azimuth direction at both sides in the example in the diagram according to the difference of the element position on the element of interest (difference with the position of the center element), unprocessed element data for three elements are superimposed and determined as one superimposition processed element data for the element of interest.

The superimposed element data of the element of interest obtained in this manner is illustrated in FIG. 7F.

The element data of the element of interest illustrated in FIG. 7D is ghost element data. Therefore, even when phase matching is performed by performing delay time correction and azimuth direction shifting on the unprocessed element data of the adjacent element on both sides of the element data of the element of interest, as illustrated in FIG. 7F, each element data of the adjacent element and the element data of the element of interest do not overlap because the phases are not mutually matched. For this reason, because the phases do not match even when, for example, three element data are added, signals or the like where the phases are inverted cancel each other out, thus the added value is not large and, for example, a small value is indicated when the average value is determined by averaging.

In relation to the other element data, FIG. 7G illustrates a superimposed state of three adjacent element data for each of five element data in the example in the diagram as a result of performing the same delay time correction and azimuth direction shifting as for the element data of the element of interest. With respect to these, FIG. 7H illustrates the results after, for example, addition processing or averaging processing is carried out as the superimposition processing.

As illustrated in FIG. 7H, in a case where a center element where the reflection point is present directly below illustrated in FIG. 7A is the element of interest, the element data of the true signal is determined as superimposition processed element data having a high brightness value. In contrast, in all four element data of each of the two element data on both sides thereof, for the ghost element data, the element data where the phases do not match each other are added or averaged. Therefore, because the element data cancel each other out, the value of the ghost superimposition processed element data is lower than that of the superimposition processed element data having a high brightness value which is element data of a true signal, and it is possible to reduce the influence of the ghost element data on the true element data, or it is possible to reduce the influence thereof to a level which may be ignored.

That is, one or more of the element data which is obtained by transmission and reception of the ultrasonic waves for which the transmission regions of the ultrasonic beam overlap and for which the center elements are different are superimposed on element data (element data of the element of interest) where a certain element is set as the element of interest and which is obtained by transmission of an ultrasonic beam where this element of interest is the center element by performing time and azimuth direction position matching, and processed element data corresponding to the element data of the element of interest is generated. Accordingly (in other words, by performing rebuilding (correction) of the element data of the element of interest using element data according to transmission and reception where at least a portion of the ultrasonic beam overlap and the center element is different), the brightness level of the true element data is increased and it is possible to decrease the ghost element data.

Therefore, because it is possible to generate the ultrasound image with element data such that the influence of the ghost is eliminated, that is, the focus points at all points on the sound ray are linked by performing phasing addition or detection processing on the processed element data, generating the reception data, and generating the ultrasound image, it is possible to generate an ultrasound image with high image quality, high brightness, and excellent sharpness.

Here, the generation of the processed element data is also referred to as multi-line processing in the following description.

In the present invention, the center element is the element in the center in the azimuth direction in a case where the number of openings of the transmission (the number of elements which perform the transmission of the ultrasonic waves) is an odd number.

On the other hand, in a case where the number of openings is an even number, any one of the elements in the center in the azimuth direction is set as the center element, or, assuming that there is an element in the middle of the azimuth direction, this element is set to be the center element. That is, in the case where the number of openings is an even number, a calculation may be performed with the assumption that there is a focus point on a line in the middle of the openings.

Here, as the superimposition processing method in the superimposition processor 49, an average value or a median value may be taken instead of only adding, or addition may be carried out after multiplication with a coefficient. Here, taking the average value or the median value may be considered equivalent to applying an averaging filter or a median filter at the element data level; however, an inverse filter or the like which performs normal image processing may also be applied instead of the averaging filter or the median filter.

Alternatively, when each of the element data to be superimposed is compared, the value is the maximum in a case where the element data are similar, the value is average in a case where the element data are not similar, and the value is intermediate in a case where the distribution is biased, but the superimposition processing may be changed on the basis of the feature amount of each of the element data to be superimposed without being limited thereto.

In addition, the number of element data to be superimposed on the element data of the element of interest is not limited to two in the example in the diagram and may be one or may be three or more. That is, the number of the element data to be superimposed on the element data of the element of interest may be appropriately set according to the required processing speed (the frame rate or the like), image quality, or the like.

Here, it is desirable that the number of element data to be superimposed on the element data of the element of interest match the extent of the spread of the beam width of the ultrasonic beam. Accordingly, in a case where the beam width changes according to the depth, the number of the element data to be superimposed may also be changed according to the depth.

In addition, because the beam width depends on the number of transmission openings, the number of element data to be superimposed may be changed according to the number of the transmission openings. Alternatively, the number of element data to be superimposed may be changed on the basis of the feature amount such as the brightness value of the image and, in addition, the optimum number of element data to be superimposed may be selected from an image created by changing the number of element data to be superimposed into a plurality of patterns.

Here, in the multi-line processing above, the processed element data of the element data of the element of interest is generated by superimposing the element data where the center elements are different and which is obtained by a transmission of a plurality of ultrasonic beams for which the transmission direction of the ultrasonic beams is parallel (the angles are the same); however, the present invention is not limited thereto.

For example, the processed element data may be generated by superimposing the element data where the center elements are the same and which is obtained by the transmission of a plurality of ultrasonic beams where the transmission directions (angles) are different. At this time, whether to generate the processed element data of the element data obtained by the transmission of any ultrasonic beam (that is, whether to generate the processed element data of the sound ray in any direction) may be set by default according to the examination site, the type of probe, or the like, or may be selected by the operator.

In addition, the processed element data may be generated using both of the element data where the center elements are different and which is obtained by the transmission of parallel ultrasonic beams and the element data where the center elements are the same and which is obtained by the transmission of ultrasonic beams with different transmission directions.

As described above, the element data processor 22 sends the generated processed element data to the image generator (the phasing addition section 38).

In the image generator 24 to which the processed element data is supplied, as described above, the reception data is generated by performing a reception focusing process by the phasing addition section 38 performing phasing addition on the processed element data and the detection processor 40 generates B mode image data by performing attenuation correction processing and envelope detection processing on the reception data.

In addition, in the image generator 24, the DSC 42 raster converts the B mode image data into image data corresponding to a normal television signal scanning method and performs a predetermined process such as a gradation process in the image processor 44.

The image processor 44 stores generated B mode image data in the image memory 46 and/or sends the generated B mode image data to the display controller 26 to display a B mode image of the subject on the monitor 28.

Next, more detailed description will be given of the method for setting the transmission frequency in the frequency setting section 17.

First, description will be given of a relationship between the transmission frequency of the ultrasonic waves and the time difference between the (ghost) element data to be superimposed in the superimposition processor 49. Here, for the sake of simplicity in the following example, description will be given of superimposing two pieces of element data.

Figure 8A:
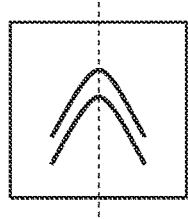
FIGS. 8A to 8C are conceptual diagrams for illustrating a relationship between a transmission frequency and a superimposition time difference.

As an example, FIG. 8A is a diagram in which, out of an element data group illustrated in FIG. 7D, the center element of the element data to the left of the element data in the middle is set as the element of interest and the element data on the left side thereof is superimposed thereon. That is, FIG. 8A illustrates a state in which delay time correction is performed on the element data on the left side and two pieces of element data are superimposed by shifting by one element in the azimuth direction.

As illustrated in FIG. 8A, because the element data of the element of interest in FIG. 8A is ghost element data, even when phase matching is performed by performing delay time correction and azimuth direction shifting, the element data do not overlap because the phases of each of the element data of the adjacent element and the element data of the element of interest do not match each other.

Figure 8B:
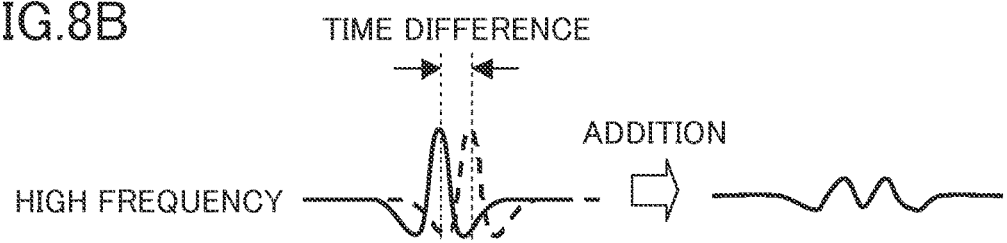
Figure 8C:
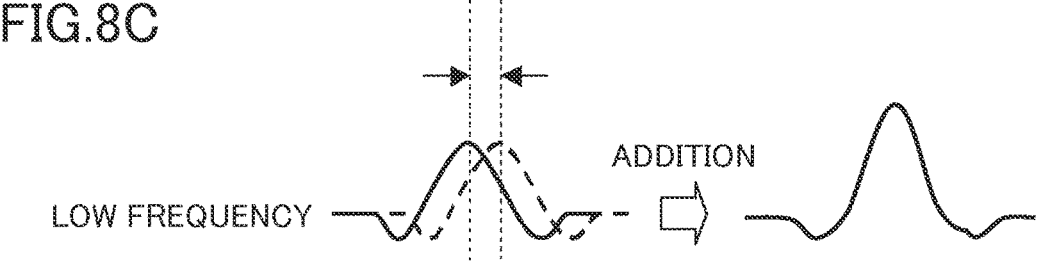

FIG. 8B and FIG. 8C are diagrams schematically illustrating the signal on a line (center element line) illustrated by a broken line in FIG. 8A. That is, in FIG. 8B and FIG. 8C, the horizontal axis is the time and the vertical axis is the signal strength.

Here, FIG. 8B illustrates a case where the half cycle of the ultrasonic waves is a transmission frequency which is shorter than the time difference in the reception time between the element data to be superimposed. On the other hand, FIG. 8C illustrates a case where the half cycle of the ultrasonic waves is a transmission frequency which is longer than the time difference in the reception time between element data to be superimposed.

As illustrated in FIG. 8B, in a case where the half cycle of the ultrasonic waves is a transmission frequency which is shorter than the time difference in the reception time between element data to be superimposed, when addition processing (averaging processing) is carried out, the phases are canceled out because the phases are shifted in relation to each other and the signal is attenuated as illustrated on the right side in the diagram. That is, it is possible to eliminate the ghost signal.

On the other hand, as illustrated in FIG. 8C, in a case where the half cycle of the ultrasonic waves is a transmission frequency which is longer than the time difference in the reception time between element data to be superimposed, the signal is strengthened when the addition processing (averaging processing) is carried out as illustrated on the right side in the diagram because the phases are not sufficiently shifted between the signals. That is, it is not possible to eliminate the ghost signal.

Accordingly, in the present invention, the frequency setting section 17 sets the transmission frequency where the half cycle is shorter than the time difference according to the time difference in the reception time between the element data to be superimposed, and supplies information on the set transmission frequency to the transmitter 14. By superimposing the element data obtained by performing the transmission with the set transmission frequency, the ghost signals are appropriately eliminated.

Next, description will be given of the time difference in the reception time between the element data using FIG. 9.

Figure 9:
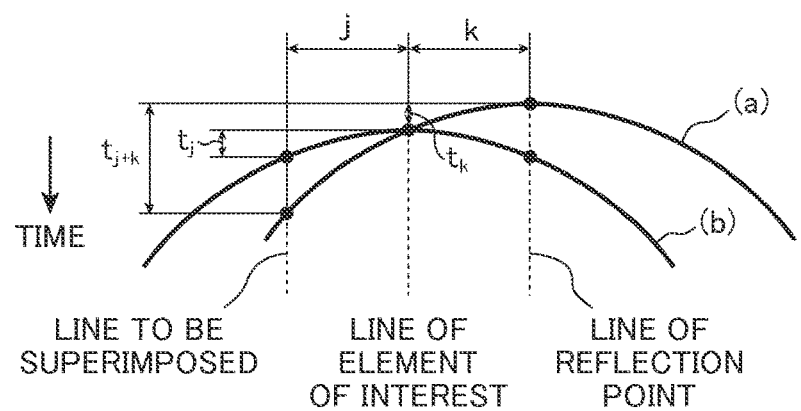
FIG. 9 is a conceptual diagram for illustrating a time difference in the reception time between element data.

In the same manner as FIG. 7B, the curved line denoted by (a) in FIG. 9 illustrates an example of the delay time in a case where an element located directly above a reflection point is the element of interest. In addition, in the same manner as FIG. 7E, the curved line denoted by (b) in FIG. 9 illustrates an example of the delay time in a case where an element at a position shifted from the reflection point is the element of interest.

The reflection point is located on a line where the element separated by k elements from the element of interest is set as the center element and element data acquired by setting the element separated by j elements from the element of interest as the center element is superimposed. When the delay time in a case of the center element being separated by x elements from the element of interest is set as $t_x$, from the curved line (a), the time difference in the reception time between the signal corresponding to the reflection point on the element data corresponding to the element of interest and the signal corresponding to the reflection point on the element data to be superimposed, before performing delay time correction is $t_{j+k}-t_k$. In a case where delay time correction is performed on the basis of the element of interest, correction with the delay time $t_j$ is performed with respect to the element data to be superimposed using the delay time indicated by the curved line (b). Accordingly, the time difference t in the reception time between the signal corresponding to the reflection point on the element data corresponding to the element of interest and the signal corresponding to the reflection point on the element data to be superimposed after performing delay time correction on the basis of the element of interest is $t=t_{j+k}-t_k-t_j$.

As described above, the delay time indicated by the curved lines (a) and (b) in FIG. 9 can be calculated in advance in the delay time calculator 48 on the basis of information such as the element spacing or focus point positions of the ultrasonic beams, the positions of the sampling points, the transmission openings, and the reception openings. Accordingly, the time difference t in the reception time between the element data to be superimposed can also be calculated in advance.

The frequency setting section 17 acquires information, which is input from the operating section 32 or input from the operating section 32 and stored in the storage unit 34, relating to the probe 12 (ultrasound transducer (element)), the focus point position of the ultrasonic beam, the transmission openings and reception openings of the probe 12, and the like. Then, the frequency setting section 17 calculates the time difference t in the reception time between the element data to be superimposed on the basis of the information on the delay time supplied from the delay time calculator 48.

Next, the frequency setting section 17 sets a transmission frequency where the half cycle is shorter than the calculated time difference t. The frequency setting section 17 supplies information on the set transmission frequency to the transmitter 14.

The transmitter 14 transmits ultrasonic beams at the set transmission frequency. The element data processor 22 performs multi-line processing using the element data obtained by transmitting the ultrasonic beams at the set transmission frequency.

As described above, in a normal ultrasound diagnostic apparatus, it is known that, when transmitting ultrasonic beams, as the transmission frequency is increased, the distance resolution is improved, but there is a greater degree of attenuation. That is, it is known that although the image quality is better as the transmission frequency is higher, there is a decrease in sensitivity. Accordingly, a transmission frequency which is suitable for the region (depth) to be viewed is set according to the purpose.

However, in ultrasound diagnostic apparatuses that performs multi-line processing, the transmission of the ultrasonic beams at a transmission frequency suitable for the multi-line processing has not been considered.

With respect to this, the present inventors have found problems in that, while performing the multi-line processing in the ultrasound diagnostic apparatus, when the cycle of the transmission frequency is large with respect to the time difference in the reception time between the data to be superimposed, the superimposition cannot be appropriately performed and the data is emphasized by overlapping even for the ghost signals and it is not possible to eliminate the ghost signals.

The ultrasound diagnostic apparatus 10 of the present invention sets the transmission frequency of the ultrasonic beams according to the processing conditions of the multi-line processing when generating second element data corresponding to any of the first element data from a plurality of first element data, that is, when performing the multi-line processing, and generates the second element data (processed element data) by using the plurality of first element data (unprocessed element data) obtained by transmitting the ultrasonic beams at the transmission frequency set in the frequency setting section.

Accordingly, because the element data can be appropriately superimposed when superimposing the element data, it is possible to prevent the ghost signals from being emphasized. Accordingly, the effect of the multi-line processing can be reliably exhibited and high quality ultrasound images can be obtained.

In addition, in the imaging of normal ultrasound images, when imaging a deep position at a high transmission frequency, the attenuation of the ultrasonic waves is increased and the sensitivity is decreased; however, because performing the multi-line processing has an effect of emphasizing the true signals, the imaging can be carried out at a higher transmission frequency even at deep positions and higher quality ultrasound images can be obtained.

Here, in a case where the probe 12 is configured to be able to switch a plurality of different transmission frequencies, the frequency setting section 17 may select and set any transmission frequency where the half cycle is shorter than the calculated time difference t. In addition, in a case where the probe 12 is able to linearly change the transmission frequency, any value may be used as long as the transmission frequency is a transmission frequency where the half cycle is shorter than the calculated time difference t. In any case, the value to be selected may be appropriately determined according to the depth of the region to be imaged, the performance of the probe 12, the required image quality of the ultrasound image, and the like.

Here, as understood from FIG. 8B, when the half cycle is excessively short with respect to the time difference t (when the transmission frequency is excessively high), because the peak portions and valley portions in the signals do not overlap, the effect of canceling out the signals is reduced. However, because the distance resolution is improved as the transmission frequency is increased, the transmission frequency is preferably determined in consideration of these effects.

In addition, when determining the time difference t in the reception time, it is not necessary to know the position (on the line) of the reflection point. As can be understood from FIG. 9, for the time difference t in the reception time, the time difference t is smaller as the position (line) of the reflection point is closer to the line of the element of interest. Accordingly, the time difference t may be determined assuming that the reflection point is on the line of the element adjacent to the element of interest.

In addition, in a case where a plurality of element data are superimposed, the transmission frequency may be set on the basis of the time difference t in the reception time between any of the element data. From the point of view of image quality, the transmission frequency is preferably set on the basis of the time difference t in the reception time with the element data of the element at the closest position; however, a high transmission frequency is necessary. On the other hand, on the basis of the time difference t with the element data of the element at the furthest position, the range of the transmission frequencies which can be adopted is increased; however, the effect of improving the image quality is reduced.

In addition, as understood from FIG. 6A, FIG. 6B, and the like, the time difference between the element data changes according to the depth (position of the sampling point in the depth direction) of the region to be viewed. In a case where it is desirable to obtain the effect of the multi-line processing at any depth, a transmission frequency with a half cycle shorter than the shortest time difference t may be adopted. In addition, in a case where it is desirable to view a specific depth, the transmission frequency may be set on the basis of the time difference t at this depth.

Figure 10:
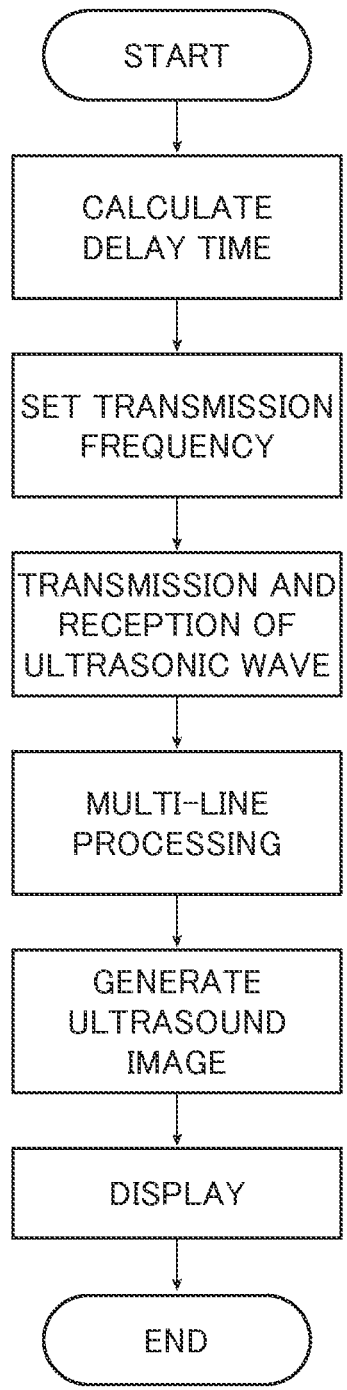
FIG. 10 is a flow chart for illustrating an operation of the ultrasound diagnostic apparatus illustrated in FIG. 1.

Detailed description will be given below of the signal processing method (the signal processing method of the present invention) in the ultrasound diagnostic apparatus 10 with reference to the flow chart illustrated in FIG. 10.

The program of the present invention is a program for causing a computer in the ultrasound diagnostic apparatus 10 to execute the signal processing method below.

In addition, the recording medium of the present invention is a recording medium on which the program described above is recorded. For example, the recording medium may be a memory which stores the program described above and which is attached to the controller or the like. Alternatively, the recording medium may be a memory medium (removable medium) configured to be inserted into and removed from an ultrasound inspection apparatus, such as a CD-ROM, or may be configured such that the program described above is read by a diagnostic apparatus via an interface corresponding to the removable medium.

In the ultrasound diagnostic apparatus 10, first, the delay time calculator 48 calculates the delay time of the element data on the basis of the information on the probe 12 (element spacing) input from the operating section 32, the focus point position of the ultrasonic beams, the transmission openings, the reception openings, the position of the sampling points, the number of the element data to be superimposed, or the like.

Next, the frequency setting section 17 sets the transmission frequency on the basis of information on the calculated delay time.

In order to acquire the element data according to instructions from the controller 30, the transmitter 14 transmits the ultrasonic beam to the subject by driving (with a predetermined number of openings and opening positions) the ultrasonic transducers (elements) corresponding to the probe (transducer array 36) at the set transmission frequency, and the ultrasound echoes reflected by the subject are received by the ultrasound transducer (element) and analog reception signals are output to the receiver 16.

The receiver 16 performs a predetermined process such as amplification on the analog reception signal and supplies the result to the A/D converter 18.

The A/D converter 18 analog-to-digital converts the analog reception signal supplied from the receiver 16 and sets the signal as element data constituted by a digital reception signal.

The element data is stored in the element data storage 20.

When the acquisition of the element data for all the lines is finished, the element data processor 22 generates processed element data by performing the multi-line processing.

Specifically, as illustrated in FIGS. 7A to 7H described above, for the element of interest and both elements adjacent thereto, the element data processor 22, for example, calculates the delay time of the element data of both adjacent elements with respect to the element data of the element of interest, performs delay time correction and shifting in the azimuth direction on the element data of the adjacent elements, and generates processed element data of the element of interest by superimposing the element data of the elements adjacent to both sides on the element data of the element of interest. At this time, because the element data is data acquired by transmission and reception at a transmission frequency with a half cycle shorter than the time difference t of the delay time between the element data, as illustrated in FIG. 8B, the ghost signals are prevented from being emphasized by shifting and superimposing the signals, and the superimposition can be appropriately performed.

The element data processor 22 generates a plurality of processed element data by performing the superimposition of the element data with respect to each of the element data corresponding to a predetermined plurality of lines. The element data processor 22 supplies the generated processed element data to the image generator 24. The image generator 24 generates ultrasound images (B mode image data) using the processed element data. At this time, it is possible to obtain a high quality ultrasound image because appropriately superimposed processed element data is used.

Here, in the first embodiment described above, the frequency setting section 17 is configured to set the transmission frequency by determining the time difference t in the reception time between the element data to be superimposed on the basis of the delay time calculated by the delay time calculator 48; however, the present invention is not limited thereto and the transmission frequency may be set on the basis of the conditions for determining the delay time.

Figure 11:
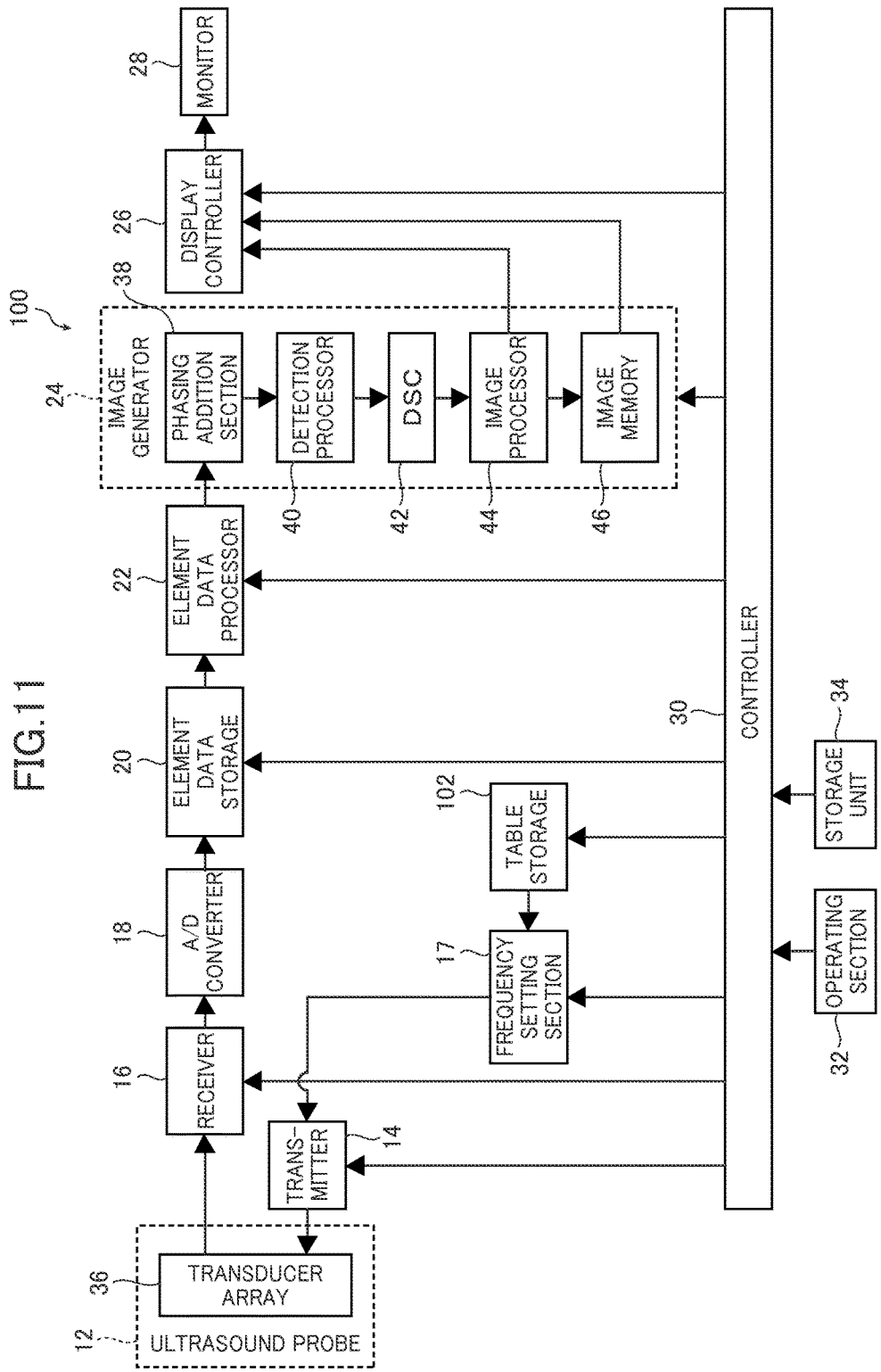
FIG. 11 is a block diagram conceptually illustrating another example of the configuration of the ultrasound diagnostic apparatus of the present invention.

FIG. 11 is a block diagram conceptually illustrating an example of a configuration of an ultrasound diagnostic apparatus of the second embodiment of the present invention.

Here, because an ultrasound diagnostic apparatus 100 illustrated in FIG. 11 has the same configuration as the ultrasound diagnostic apparatus 10 illustrated in FIG. 1 except for having a table storage 102, the same reference numerals will be given to the same constituent components and the details thereof will be omitted.

The table storage 102 is a part for storing the relationship between at least one of information on the element arrangement, the sound velocity, the focus point position, the position of the sampling point (the depth of the region to be viewed), the lines to be superimposed, and the like, and the transmission frequency, as a frequency table in advance.

As illustrated in FIG. 9, the time difference t in the reception time between the element data is determined from the delay time. In addition, the delay time is calculated from the sound velocity, the transmission elements, the focus point positions of the ultrasonic beams, the positions of the sampling points, and the geometric arrangement of the reception elements. Accordingly, at least one of the sound velocity, the element arrangement, the focus point position, and the position of the sampling point can be associated with the transmission frequency where the half cycle is shorter than the time difference t in the reception time.

Here, the frequency table may be created in advance by calculating the time difference t with the same method as in the first embodiment. Alternatively, the frequency table may be created by creating an ultrasound image by changing the transmission frequency, determining the transmission frequency where the image quality of the ultrasound image is improved, and associating this transmission frequency with information on the sound velocity, the element arrangement, the focus point position, and the position of the sampling point.

Information for the element data processor 22 to perform the superimposition processing on the element data is supplied from the controller 30 to the frequency setting section 17. That is, the frequency setting section 17 acquires at least one of information on the element arrangement, the sound velocity, the focus point position, the position of the sampling point, and the like.

Next, the frequency setting section 17 reads out the frequency table stored in the table storage 102 and sets the transmission frequency on the basis of the read-out information and the frequency table.

When the transmission frequency is set, the transmitter 14 transmits ultrasonic beams to the inside of the subject by driving the ultrasound transducers at a set transmission frequency according to instructions from the controller 30. The element data processor 22 performs multi-line processing using the element data obtained by transmitting the ultrasonic beams at the set transmission frequency. Accordingly, during the multi-line processing, the ghost signals are prevented from being emphasized and the superimposition can be appropriately performed.

In addition, the first embodiment has a configuration in which the element data processor 22 sets the transmission frequency according to the processing conditions; however, the present invention is not limited thereto and may have a configuration in which the transmission frequency is switched by switching between a mode for performing the multi-line processing and a mode for performing the normal processing.

Figure 12:
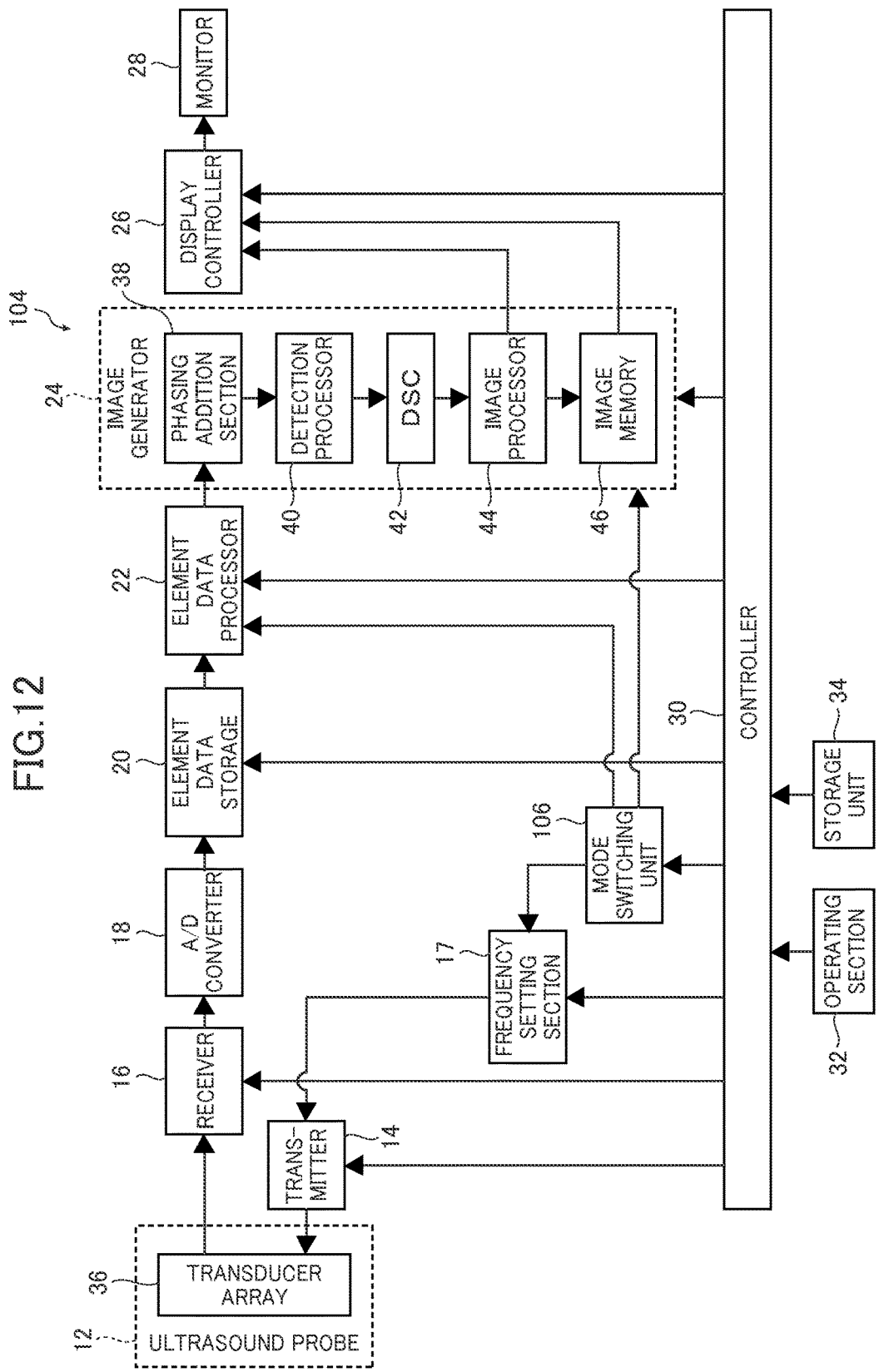
FIG. 12 is a block diagram conceptually illustrating another example of the configuration of the ultrasound diagnostic apparatus of the present invention.

FIG. 12 is a block diagram conceptually illustrating an example of a configuration of an ultrasound diagnostic apparatus of the third embodiment of the present invention.

Here, because an ultrasound diagnostic apparatus 104 illustrated in FIG. 12 has the same configuration as the ultrasound diagnostic apparatus 10 illustrated in FIG. 1 except for having a mode switching unit 106, the same reference numerals will be given to the same constituent components and details thereof will be omitted.

The mode switching unit 106 generates processed element data by the element data processor 22 performing the multi-line processing on the first element data read out from the element data storage 20 according to input from the operating section 32 or instructions from the controller 30 and switches between a multi-line mode in which the image generator 24 generates ultrasound images from the processed element data and a normal mode in which the image generator 24 generates ultrasound images from the first element data read out from the element data storage 20 without performing processing in the element data processor 22.

The mode switching unit 106 supplies information on the mode to the frequency setting section 17 and the element data processor 22.

The frequency setting section 17 switches the transmission frequency according to the information on the mode supplied from the mode switching unit 106.

The frequency setting section 17 has no particular limitation on the values of the transmission frequencies to be switched and various transmission frequencies to be used in each of the multi-line mode and the normal mode may be set. For example, in the multi-line mode, a transmission frequency determined with the same method as the first embodiment may be set. Alternatively, in advance, in each of the multi-line mode and the normal mode, the optimum transmission frequency may be determined by experiments and the transmission frequencies may be set according to the switching of the mode.

In addition, the first embodiment is configured such that the multi-line processing is performed in the element data processor 22 using element data; however, the present invention is not limited thereto and may be configured to perform the multi-line processing on first reception data which is first element data subjected to phasing addition.

Figure 13:
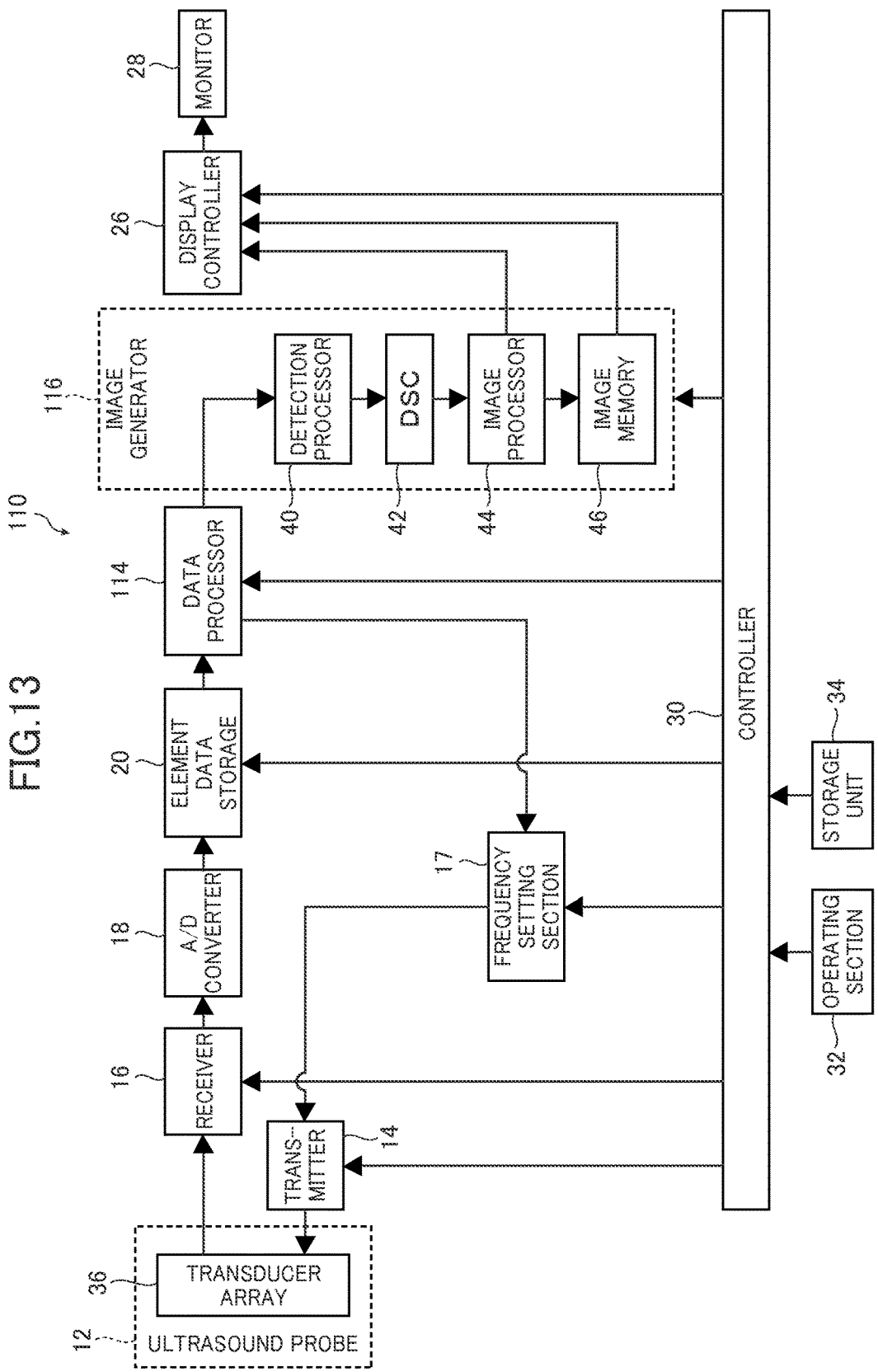
FIG. 13 is a block diagram conceptually illustrating another example of the configuration of the ultrasound diagnostic apparatus of the present invention.

FIG. 13 is a block diagram conceptually illustrating an example of an ultrasound diagnostic apparatus 110 which is the fourth embodiment of the present invention.

Here, because the ultrasound diagnostic apparatus 110 illustrated in FIG. 13 has the same configuration as the ultrasound diagnostic apparatus 10 illustrated in FIG. 1 except for having a data processor 114 instead of the element data processor 22 and having an image generator 116 instead of the image generator 24, the same reference numerals are given to the same constituent components and detailed description thereof will be omitted.

The ultrasound diagnostic apparatus 110 has the ultrasound probe 12, the transmitter 14 and the receiver 16 connected with the ultrasound probe 12, the frequency setting section 17, the A/D converter 18, the element data storage 20, the data processor 114, the image generator 116, the display controller 26, the monitor 28, the controller 30, the operating section 32, and the storage unit 34.

Figure 14:
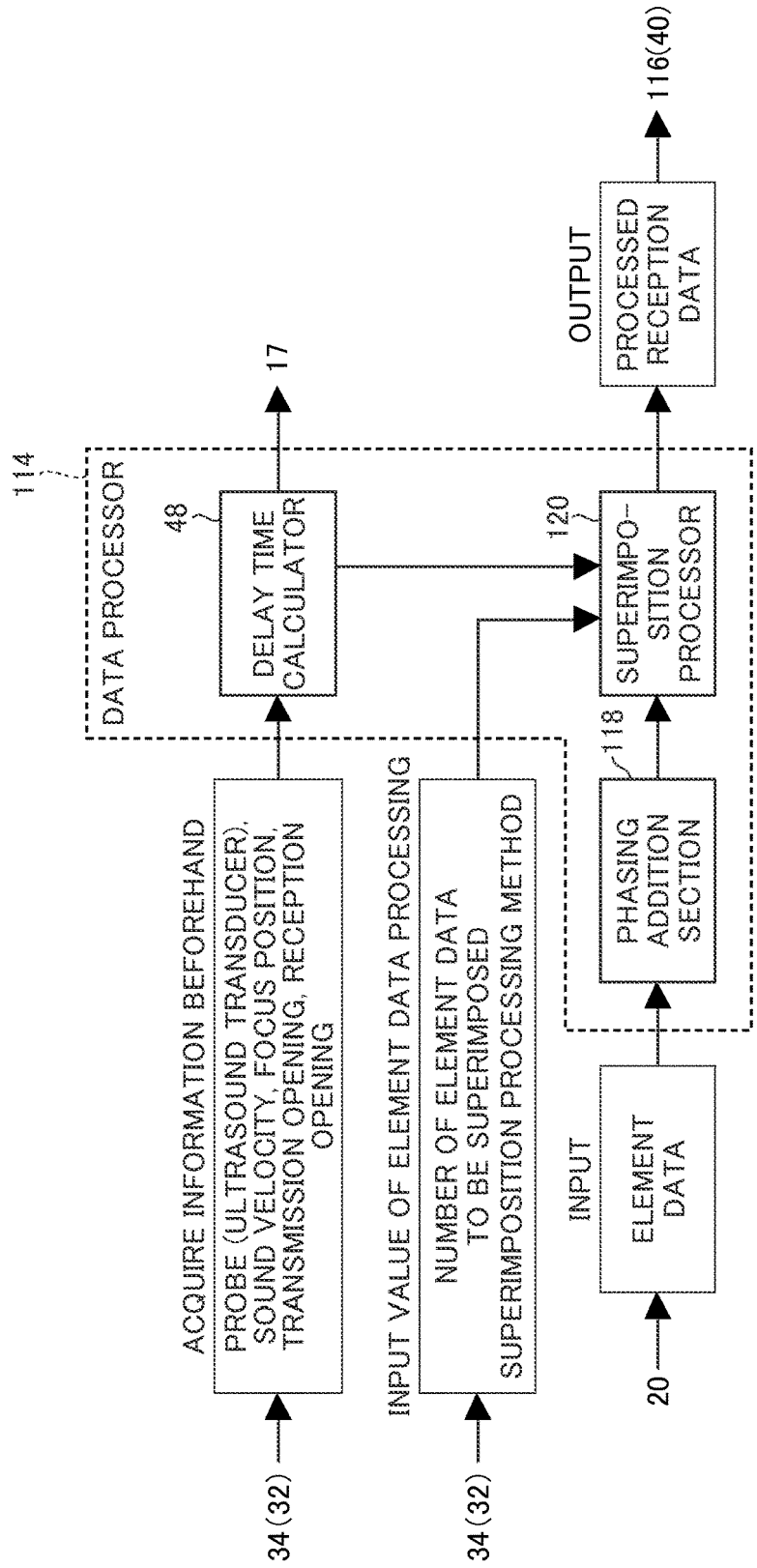
FIG. 14 is a block diagram conceptually illustrating an example of the configuration of a data processor of the ultrasound diagnostic apparatus illustrated in FIG. 13.

FIG. 14 is a block diagram conceptually illustrating the configuration of the data processor 114.

The data processor 114 has a phasing addition section 118, the delay time calculator 48, and a superimposition processor 120.

The phasing addition section 118 performs reception focusing processing by performing phasing addition on the element data read out from the element data storage 20 and generates first reception data.

Here, the phasing addition section 118 performs phasing addition for each of a plurality of element data to be superimposed by the superimposition processor 120 to be described below on the basis of the same element (line).

The superimposition processor 120 acquires first reception data generated by the phasing addition section 118 by reading out the element data from the element data storage 20 on the basis of the information relating to the data processing, such as the number of data to be superimposed and the superimposition processing method.

In addition, on the basis of the delay times corresponding to each of the reception data calculated by the delay time calculator 48, the superimposition processor 120 generates processed (second) reception data by superimposing two or more pieces of the first reception data in terms of the reception time, that is, by matching the times.

More detailed description will be given of the phasing addition section 118 and the superimposition processor 120 using FIG. 15 and FIGS. 16A to 16C.

Figure 15:
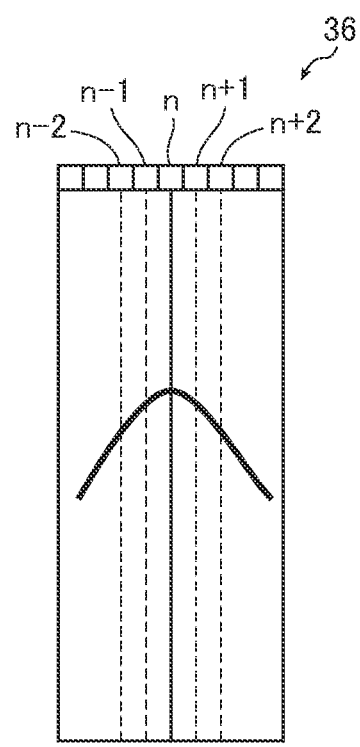
FIG. 15 is a diagram conceptually illustrating element data and elements.

FIG. 15 conceptually illustrates element data and the transducer array 36 at positions corresponding thereto.

The element data illustrated in FIG. 15 is element data obtained by performing the transmission and reception of ultrasonic waves with the n-th element set as the center element.

In the following description, for example, the reception data generated by performing phasing addition with respect to the n-th element data on the basis of the n−2th line is represented as n(n−2)th reception data. That is, the reception data obtained by performing phasing addition on the n-th element data on the basis of the i-th line is represented as n(i)th reception data.

FIGS. 16A to 16C are diagrams for illustrating phasing addition by the phasing addition section 118 and superimposition processing by the superimposition processor 120.

FIG. 16A illustrates each of n−2th element data, n−1th element data, and n-th element data.

As an example, a case of generating processed reception data corresponding to the n-th reception data using the n−2th, n−1th, and n-th reception data will be considered.

In a case where processed reception data corresponding to the n-th reception data is generated, the phasing addition section 118 performs phasing addition for each of the element data on the basis of the n-th element. That is, phasing addition is performed on each of the element data on the basis of the lines illustrated by solid lines in the diagram. The phasing addition generates first reception data (n−2(n)th reception data, n−1(n)th reception data, and n(n)th reception data) illustrated in FIG. 16B.

Next, for the first reception data generated by the phasing addition section 118, the superimposition processor 120 generates processed reception data corresponding to the n-th reception data as illustrated in FIG. 16C by superimposing each first reception data by matching the time on the basis of the delay time corresponding to each of the reception data calculated by the delay time calculator 48.

The data processor 114 supplies the processed reception data to the image generator 116.

The image generator 116 has the detection processor 40, the DSC 42, the image processor 44, and the image memory 46.

In the image generator 116, the detection processor 40 generates B mode image data by performing attenuation correction processing and envelope detection processing on the reception data. Furthermore, the DSC 42 raster converts the B mode image data into image data corresponding to a normal television signal scanning method and performs predetermined processing such as gradation processing in the image processor 44.

The image processor 44 stores generated B mode image data in the image memory 46 and/or sends the generated B mode image data to the display controller 26 to display a B mode image of the subject on the monitor 28.

The ultrasound diagnostic apparatus, the signal processing method, and the program of the present invention have been described above; however, the present invention is not limited to the examples described above and various improvements or modifications may be made within a range which does not depart from the gist of the present invention as a matter of course.

For example, in order to perform the multi-line processing without the element data storage 20 which stores element data for one image, the transmission and reception of the ultrasonic waves may be performed every time or a plurality of times as necessary corresponding to one element of interest.

What is claimed is:

1. An ultrasound diagnostic apparatus configured to inspect an inspection object using an ultrasonic beam, the apparatus comprising:
    a probe having a plurality of elements arranged therein, the probe being configured to transmit the ultrasonic beam and receive an ultrasonic echo reflected by the inspection object, and to output an analog element signal according to the received ultrasonic echo;
    a transmitter configured to cause the probe to transmit the ultrasonic beam a plurality of times using at least two of the plurality of elements as transmission elements so as to form a predetermined transmission focus point;
    a receiver configured to receive analog element signals output by at least two of the plurality of elements that, as reception elements, have received the ultrasonic echo corresponding to individual transmission of the ultrasonic beam and to perform a predetermined process;

an analog-to-digital converter configured to analog-to-digital convert the analog element signals processed by the receiver into first element data formed by a digital element signal;

a data processor configured to superimpose at least one of other first element data on a first element data of interest, and generate second element data; and a frequency setting section configured to set a transmission frequency of the ultrasonic beam;

wherein the analog-to-digital converter, the data processor, and the frequency setting section are configured by a central processing unit (CPU) and an operation program or a digital circuit;

one of the first element data is data obtained by analog-to-digital converting a plurality of analog element signals that are output from the plurality of elements after the transmitter causes the plurality of elements to transmit the ultrasonic beam once and the plurality of elements receive the ultrasonic echo;

the transmitter and the receiver transmit and receive ultrasonic waves a plurality of times, and the analog-to-digital converter generates a plurality of first element data corresponding to a plurality of transmissions and receptions;

the second element data is data generated before phasing addition;

the data processor performs addition processing or averaging processing as superimposition processing of the plurality of first element data;

the data processor generates a plurality of second element data by changing the first element data of interest a plurality of times;

the frequency setting section sets the transmission frequency of the ultrasonic beam according to a processing condition in the data processor; and the data processor generates the second element data using the plurality of first element data obtained by the transmitter transmitting the ultrasonic beam with the transmission elements at the transmission frequency set in the frequency setting section.

2. The ultrasound diagnostic apparatus according to claim 1, wherein the data processor generates the second element data by superimposing the plurality of first element data according to a reception time at which the reception elements have received the ultrasonic echo and positions of the reception elements.

3. The ultrasound diagnostic apparatus according to claim 2, wherein the frequency setting section sets the transmission frequency according to a time difference in reception time between the plurality of first element data to be superimposed by the data processor.

4. The ultrasound diagnostic apparatus according to claim 3, wherein the frequency setting section sets the transmission frequency where a half cycle thereof is shorter than the time difference.

5. The ultrasound diagnostic apparatus according to claim 1, wherein the frequency setting section sets the transmission frequency according to at least one of a measurement depth, a position of the transmission focus point, and an arrangement spacing of the transmission elements.

6. The ultrasound diagnostic apparatus according to claim 1, wherein the transmitter changes at least one of a center element and a transmission direction of the ultrasonic beam.

7. The ultrasound diagnostic apparatus according to claim 6, wherein the data processor generates the second element data using at least one of the plurality of first element data obtained by transmission of the ultrasonic beam for which the center element are different to each other and the plurality of the first element data obtained by transmission of the ultrasonic beam for which the transmission direction are different to each other.

8. The ultrasound diagnostic apparatus according to claim 1, wherein the data processor generates the second element data from the plurality of first element data obtained by transmission of the ultrasonic beam where transmission regions overlap.

9. A signal processing method for an ultrasound diagnostic apparatus for inspecting an inspection object using a probe having a plurality of elements arranged therein, the probe transmitting an ultrasonic beam, receiving an ultrasonic echo reflected by the inspection object, and outputting an analog element signal according to the received ultrasonic echo, the method comprising:

in the probe, a step of transmitting an ultrasonic beam a plurality of times so as to form a predetermined transmission focus point using at least two of the plurality of elements as transmission elements;

a step of receiving an ultrasonic echo corresponding to individual transmission of the ultrasonic beam with at least two of the plurality of elements as reception elements and outputting an analog element signal;

a step of analog-to-digital converting the analog element signal into first element data formed by a digital element signal;

a step of performing data processing for superimposing at least one of other first element data on a first element data of interest, and generating second element; and a step of setting a transmission frequency of the ultrasonic beam;

wherein one of the first element data is data obtained by analog-to-digital converting a plurality of analog element signals that are output from the plurality of elements after the step of transmitting causes the plurality of elements to transmit the ultrasonic beam once and the plurality of elements receive the ultrasonic echo;

the step of transmitting and the step of receiving ultrasonic waves are performed a plurality of times and in the step of analog-to-digital converting, a plurality of first element data corresponding to a plurality of transmissions and receptions are generated;

the second element data is data generated before phasing addition;

in the step of performing data processing, addition processing or averaging processing is performed as superimposition processing of the plurality of first element data;

a plurality of second element data are generated by performing a plurality of the step of performing data processing by changing the first element data of interest a plurality of times;

in the step of setting the transmission frequency, the transmission frequency of the ultrasonic beam is set according to a processing condition in the step of performing data processing; and in the step of performing data processing, the second element data is generated using the plurality of first element data obtained by transmitting the ultrasonic beam at the transmission frequency set in the step of setting a transmission frequency.

10. A non-transitory computer-readable recording medium having stored therein a program that causes a computer to execute a signal processing method for an ultrasound diagnostic apparatus for inspecting an inspection object using a probe having a plurality of elements arranged therein, the probe transmitting an ultrasonic beam, receiving an ultrasonic echo reflected by the inspection object, and outputting an analog element signal according to the received ultrasonic echo, the method comprising:

in the probe, a step of transmitting an ultrasonic beam a plurality of times so as to form a predetermined transmission focus point using at least two of the plurality of elements as transmission elements;

a step of receiving an ultrasonic echo corresponding to individual transmission of the ultrasonic beam with at least two of the plurality of elements as reception elements and outputting an analog element signal;

a step of analog-to-digital converting the analog element signal into first element data formed by a digital element signal;

a step of performing data processing for superimposing at least one of other first element data on a first element data of interest, and generating second element data; and a step of setting a transmission frequency of the ultrasonic beam;

wherein one of the first element data is data obtained by analog-to-digital converting a plurality of analog element signals that are output from the plurality of elements after the step of transmitting causes the plurality of elements to transmit the ultrasonic beam once and the plurality of elements receive the ultrasonic echo;

the step of transmitting and the step of receiving ultrasonic waves are performed a plurality of times and in the step of analog-to-digital converting, a plurality of first element data corresponding to a plurality of transmissions and receptions are generated;

the second element data is data generated before phasing addition;

in the step of performing data processing, addition processing or averaging processing is performed as superimposition processing of the plurality of first element data;

a plurality of second element data are generated by performing a plurality of the step of performing data processing by changing the first element data of interest a plurality of times;

in the step of setting the transmission frequency, the transmission frequency of the ultrasonic beam is set according to a processing condition in the step of performing data processing; and in the step of performing data processing, the second element data is generated using the plurality of first element data obtained by transmitting the ultrasonic beam at the transmission frequency set in the step of setting a transmission frequency.

\* \* \* \* \*